(12) United States Patent
Buchloh et al.

(10) Patent No.: US 10,105,852 B2
(45) Date of Patent: *Oct. 23, 2018

(54) TRANSPORT TOOL FOR TRANSPORTING A LABORATORY ARTICLE

(71) Applicant: Tecan Trading AG, Männedorf (CH)

(72) Inventors: Stefan Buchloh, Solothurn (CH); Thomas Iten, Zürich (CH); Nico Birkner, Pforzheim (DE)

(73) Assignee: TECAN TRADING AG, Mannedorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/628,788

(22) Filed: Feb. 23, 2015

(65) Prior Publication Data

US 2015/0239129 A1 Aug. 27, 2015

(30) Foreign Application Priority Data

Feb. 26, 2014 (CH) ........................................ 274/14

(51) Int. Cl.
| | |
|---|---|
| *B25J 15/00* | (2006.01) |
| *B25J 15/06* | (2006.01) |
| *G01N 35/00* | (2006.01) |
| *G01N 35/10* | (2006.01) |

(52) U.S. Cl.
CPC ......... *B25J 15/0047* (2013.01); *B25J 15/008* (2013.01); *B25J 15/0052* (2013.01); *B25J 15/0608* (2013.01); *G01N 35/0099* (2013.01); *G01N 35/10* (2013.01); *G01N 2035/103* (2013.01); *G01N 2035/1051* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,933,148 | A | * | 6/1990 | Perlman ................ B01L 3/0275 422/513 |
| 5,045,286 | A | * | 9/1991 | Kitajima et al. ............... 422/518 |
| 5,580,529 | A | * | 12/1996 | DeVaughn ............ B01L 3/0275 210/477 |
| 5,945,901 | A | | 8/1999 | Coleman et al. |

(Continued)

FOREIGN PATENT DOCUMENTS

| | | |
|---|---|---|
| DE | 10 2008 027306 A1 | 12/2009 |
| EP | 1361440 A1 | 11/2003 |

(Continued)

*Primary Examiner* — Brian R Gordon
(74) *Attorney, Agent, or Firm* — Notaro, Michalos & Zaccaria P.C.

(57) ABSTRACT

A transport tool for transporting a laboratory article using a pipette of a pipetting system includes at least one plug-in sleeve, which is implemented for the releasable plugging-in of a receptacle cone of a pipette, and which can be plugged onto the receptacle cone of the pipette instead of a disposable pipette tip. In addition, the transport tool includes an article holder having at least one holding part, which is implemented to form a support connection with a laboratory article. A connecting part connects the article holder to the plug-in sleeve, so that holding axes of the article holder and the sleeve axis of the plug-in sleeve are arranged coaxially or axially-parallel to one another.

14 Claims, 5 Drawing Sheets

(56) References Cited

U.S. PATENT DOCUMENTS

Figure 1A:
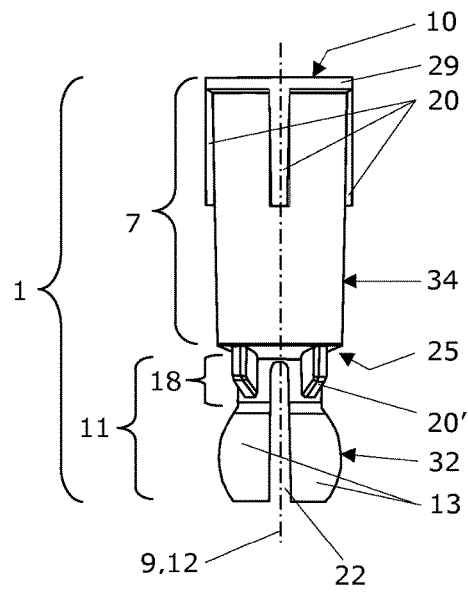

| | | | | |
|---|---|---|---|---|
| 7,033,543 | B1* | 4/2006 | Panzer | B01L 3/0279 422/525 |
| 7,452,508 | B2* | 11/2008 | Jacobs | B01F 5/10 222/251 |
| 8,163,256 | B2* | 4/2012 | Cote et al. | 422/524 |
| 8,404,116 | B2* | 3/2013 | Reiter | A61M 1/3641 210/232 |
| 8,501,118 | B2* | 8/2013 | Mathus et al. | 422/524 |
| 8,512,650 | B2* | 8/2013 | Jungheim et al. | 422/524 |
| 2004/0028564 | A1* | 2/2004 | Viot | 422/100 |
| 2008/0143098 | A1* | 6/2008 | Zimmermann | F16L 37/004 285/9.1 |
| 2010/0322826 | A1* | 12/2010 | Locascio | B01J 19/0093 422/537 |
| 2011/0076205 | A1* | 3/2011 | Kelly et al. | 422/525 |
| 2011/0136251 | A1* | 6/2011 | Astle | 436/178 |
| 2012/0121483 | A1* | 5/2012 | Pullinen et al. | 422/525 |
| 2012/0213677 | A1* | 8/2012 | Petrek | 422/525 |
| 2012/0291872 | A1* | 11/2012 | Brady | G01N 35/1065 137/3 |
| 2013/0095508 | A1* | 4/2013 | Campitelli et al. | 435/7.94 |
| 2013/0259635 | A1 | 10/2013 | Maslana et al. | |
| 2014/0045210 | A1 | 2/2014 | Menges et al. | |

FOREIGN PATENT DOCUMENTS

| | | |
|---|---|---|
| EP | 1452869 A2 | 9/2004 |
| WO | 01/16004 A1 | 3/2001 |
| WO | 2004030819 A2 | 4/2004 |

* cited by examiner

TRANSPORT TOOL FOR TRANSPORTING A LABORATORY ARTICLE

RELATED PATENT APPLICATIONS

This patent application claims priority of the Swiss patent application No. CH 00274/14 filed on Feb. 26, 2014, the whole content thereof being incorporated into the present application by explicit reference for any purpose.

RELATED FIELD OF TECHNOLOGY

The invention relates to a transport tool for transporting a laboratory article using a pipetting system for aspirating and dispensing liquids.

RELATED PRIOR ART

Pipetting systems for the automated processing of liquids are well known from prior art. Thus, for example, such a pipetting system is built and sold by the present applicant under the trade name FREEDOM EVO®. Such automated pipetting systems generally comprise one or more pipettes for aspirating and dispensing liquids into and out of various sample containers.

The use, for example, of pipette tips made of metal, which form a fixed unit with the respective pipette, is known for the operation of such pipetting systems. In particular, however, when working with liquids which contain biological materials, disposable pipette tips are preferably used, which are automatically put on to the pipettes, discarded immediately after use using a discarding mechanism, and disposed of in accordance with guidelines. In this manner, the risk of cross contaminations, for example, after multiple pipetting procedures, can be significantly reduced. Such disposable pipette tips are generally produced in this case from a cost-effective and chemically inert plastic, to compensate for the increased consumption in comparison to the fixed pipette tips. Disposable pipette tips are provided in special carriers as a standard feature. These carriers typically consist of a continuous baseplate, which is penetrated by a plurality of storage openings. A disposable pipette tip can be inserted from above into each storage opening and stored therein. Each pipette tip is held in the storage opening using reinforcement struts (or another type of widening), which are arranged on the upper end of the pipette tip, since the bottom side of each strut is applied to the top side of the carrier base. In this case, the storage openings are preferably arranged in a specific grid (array). Arranging pipette tips in the carrier in a 12×8 array is known, similarly to the number and arrangement of a 96-well standard microplate (SBS-Standard "Society for Biomolecular Screening", published by the American National Standard Institute (ANSI/SBS 1-2-3-4-2004)).

A disposable pipette tip is received in each case by a pipette, by pressing the receptacle end of a pipette into the interior of the disposable pipette tip using a defined force. The opening of the disposable pipette tips and the interior thereof are typically dimensioned so that the pipette tip is held in a friction-locked manner to form a seal on the end region or "cone" of the pipette. Alternatively, a sealing form fit or a cone having deformable O-ring can also be provided for holding the pipette tip. To release the disposable pipette tip from the pipette of the pipetting system, a corresponding counterforce is then exerted by means of a discarding mechanism on the upper collar region of the disposable pipette tip, so that it can be pushed off of the end region of the pipette and discarded.

If all disposable pipette tips of a pipette tip carrier have been consumed during operation, the empty pipette tip carrier must be removed by hand by the user and replaced with a full carrier. Alternatively, such an empty carrier can be grasped by a separate robot gripper of the pipetting system and deposited at a suitable position for disposal.

In this case, in automated laboratory devices such as the pipetting systems discussed here, it is preferable for as many steps as possible to be able to be carried out automatically, i.e., without the necessity of an intervention of a user. The use of a separate robot gripper has the danger, however, that the carrier will slip or even fall completely out of the gripper jaws onto the work surface during the gripping. Therefore, a carrier for pipette tips is proposed in document DE 10 2009 006 511, the frame of which has a waist or protruding gripping edges. Both promote form-fitted and secure gripping by a robot gripper and therefore secure and precise positioning.

Nonetheless, a separate gripping arm is necessary for gripping and transportation of the pipette tip carrier. In particular if multiple carrier plates for pipette tips are stacked one on top of another for reasons of space, this can result in problems in the gripping precision, however. In addition, the presence of such a separate robot gripping arm has the result that additional space is required, and other robotic arms of the system have less movement clearance and are therefore restricted in their usage capability.

A device for automatically carrying out immunoassays is known from document EP 1 102 994 B1. It is proposed here that instead of a robot arm for moving microplates, for example, an integral clamp be used as part of the pipetting mechanism itself. This integral clamp enables the movement of, for example, microplates between the various processing stations by the pipetting mechanism, but must be clamped in a special receptacle block, which was previously attached to a microplate to be transported or another disposable article to be transported. However, this means that all articles which are to be transported using the integral clamp must firstly be equipped with the complementary receptacle block, so that an additional expenditure of costs and time arises.

Document US 2012/0291872 A1 is considered to be the closest prior art and discloses laboratory articles and liquid handling systems and also a transport tool for transporting a laboratory article using a pipette of a pipetting system. This transport tool comprises:
a) a plug-in sleeve implemented to form a releasable plug connection with a receptacle end of a pipette of the pipetting system, this plug-in sleeve comprising an interior, a sleeve axis, and a receptacle opening, through which receptacle opening the receptacle end of a pipette of the pipetting system can be plugged into the interior of the plug-in sleeve;
b) an article holder, which comprises a holding axis and at least one holding means, which is implemented to form a support connection with a laboratory article, and
c) a connecting part, which connects the at least one article holder to the plug-in sleeve on its end opposite to the receptacle opening, so that the holding axis of the at least one article holder and the sleeve axis of the plug-in sleeve are arranged coaxially to one another.

OBJECTS AND SUMMARY OF THE PRESENT INVENTION

The object of the present invention is to propose an alternative transport tool, using which, in a simple and space-saving manner, laboratory articles can be received, transported, and deposited or discarded from the work surface of a pipetting system or from devices located on this work surface.

This object is achieved according to the features as herein disclosed, i.e. by proposing a transport tool for transporting a laboratory article using a pipette of a pipetting system. This transport tool comprises at least:
a) a plug-in sleeve implemented to form a releasable plug connection with a receptacle cone of a pipette of the pipetting system, and which comprises an interior, a sleeve axis, and a receptacle opening, wherein the receptacle cone, which is implemented to plug on a disposable pipette tip, of a pipette of the pipetting system can be plugged through the insertable opening into the interior of the plug-in sleeve, and wherein the interior of the plug-in sleeve is designed so that the transport tool can be plugged onto the receptacle cone of the pipette instead of a disposable pipette tip and can also be discarded again from the receptacle cone of this pipette;
b) an article holder, which comprises a holding axis and at least one holding means, which is implemented to form a support connection with a laboratory article, and
c) a connecting part, which connects the at least one article holder to the plug-in sleeve on its end opposite to the receptacle opening so that the holding axis (axes) of the at least one article holder and the sleeve axis of the plug-in sleeve are arranged coaxially or axially-parallel to one another.

This transport tool is characterized according to the invention in that the laboratory article is a pipette tip carrier or a microplate, wherein the at least one article holder of the transport tool is implemented to form a plug connection with a storage opening in the pipette tip carrier or with a well of the microplate. Further features according to the invention result from the dependent claims.

In addition, a method according to the invention is proposed for receiving and/or transporting and/or placing and/or discarding a laboratory article using a pipette of a pipetting system, wherein a transport tool fastenable on this pipette is used, which comprises at least:
a) a plug-in sleeve, which is implemented to form a releasable plug connection with a receptacle cone of a pipette of the pipetting system, and which comprises an interior, a sleeve axis, and a receptacle opening, through which receptacle opening end of a pipette of the pipetting system can be plugged into the interior of the plug-in sleeve, wherein the interior of the plug-in sleeve is designed so that the transport tool can be plugged instead of a disposable pipette tip onto the receptacle cone of the pipette and can also be discarded again from the receptacle cone of this pipette;
b) an article holder, which comprises a holding axis and at least one holding means, which is implemented to form a support connection with a laboratory article, and
c) a connecting part, which connects the at least one article holder to the plug-in sleeve on its end opposite to the receptacle opening so that the holding axis (axes) of the at least one article holder and the sleeve axis of the plug-in sleeve are arranged coaxially or axially-parallel to one another.

The method according to the invention is characterized in that the receptacle cone, which is implemented for plugging on a disposable pipette tip, of a pipette of the pipetting system is plugged through the receptacle opening into the interior of the plug-in sleeve of the transport tool, and that the laboratory article is a pipette tip carrier or a microplate, which is fastened on the transport tool by forming a friction-locked or form-fitted plug connection of the at least one article holder of the transport tool with at least one storage opening in the pipette tip carrier or with at least one well of the microplate.

In the context of the present invention, the term "laboratory article" is preferably understood to mean pipette tip carriers, microplates, microplate covers, covers of reagent containers or reagent troughs, covers for covering dust-sensitive gels, and the like. Carriers for microplates and holders (for example, so-called racks) for liquid containers, such as test tubes and the like, are also considered "laboratory articles". The laboratory articles, which are preferably produced from plastic by means of injection molding for reasons of low weight, good chemical resistance, and low production costs, preferably have openings (for example, storage openings for pipette tips in pipette tip carriers or wells of microplates), attached hollow cylinders, and/or flat, at least approximately horizontal surfaces. In the broadest meaning, all objects made of plastic or light metals or the combinations thereof, which are used in a pipetting system and have a total weight of less than approximately 400 g, preferably less than 200 g, are considered to be "laboratory articles".

In the context of the present invention, the term "devices" is understood to include, for example, devices for processing or studying electrophoresis gels and devices for precisely aligning microplates (for example, so-called carriers), and also further devices for storing, processing, and analyzing samples.

The transport tool according to the invention provides the following advantages over the prior art:
The necessity of integrating an additional gripper arm in the work region of the pipetting system for receiving and transporting laboratory articles is dispensed with. Therefore, more movement clearance in the work region of the pipetting system can be calculated in for the remaining gripper arms, which expands the geometry and duration of the usage options thereof.
The movement of laboratory articles for disposal or other types of repositioning can be carried out by means of the pipettes of the pipetting system provided in any case; the transport tool according to the invention functions in this case as a coupling part between pipette and laboratory article. The pipette of the pipetting system can thus itself be used as a gripper replacement.
The transport tool according to the invention can also be released again from the pipette using the already provided discarding mechanism for pipette tips. The entire operation of receiving a transport tool and a laboratory article up to repositioning the transport tool with suspended laboratory article and discarding or depositing a transport tool/laboratory article combination at a predetermined location can thus be performed completely automatically and therefore without engagement or monitoring of a user.
If the transport tool is produced as a disposable article and is also used as such, it does not have to be separated from the laboratory article for reuse, but rather can be disposed of together with the laboratory article.
If the laboratory article is an empty pipette tip carrier, for example, it can thus be received, transported, and supplied to disposal, after the use and disposal of the disposable pipette tips, using the same pipette of the pipetting system, using which the pipette tips were also received.

BRIEF INTRODUCTION OF THE ATTACHED DRAWINGS

Figure 1B:
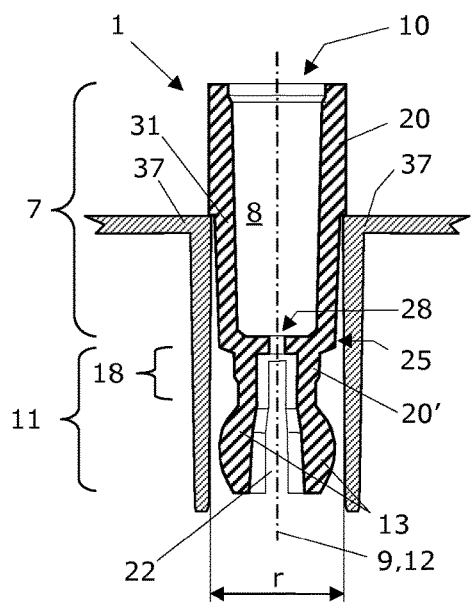
Figure 2:
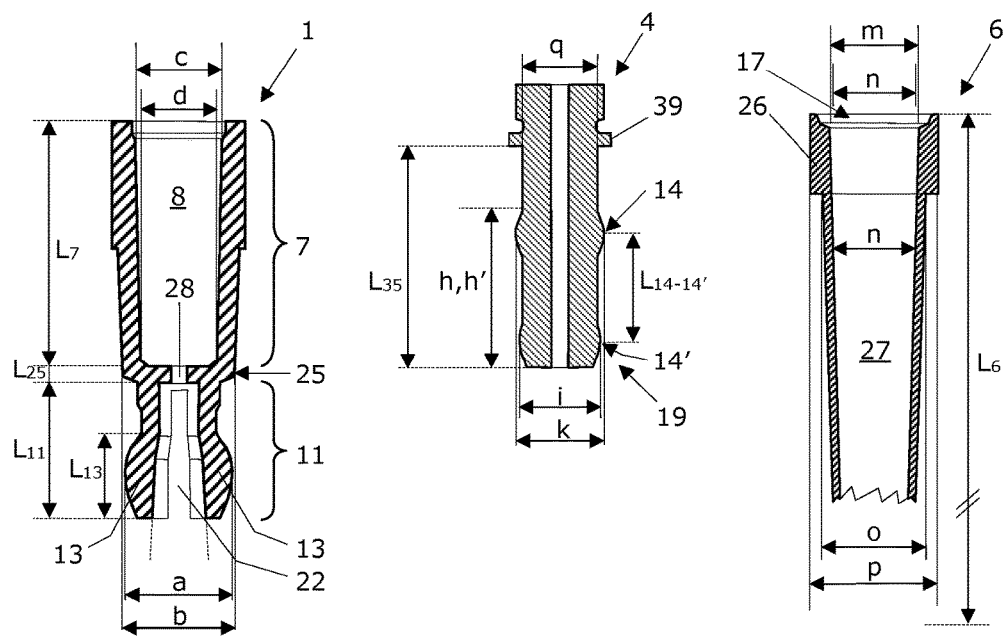
Figure 3:
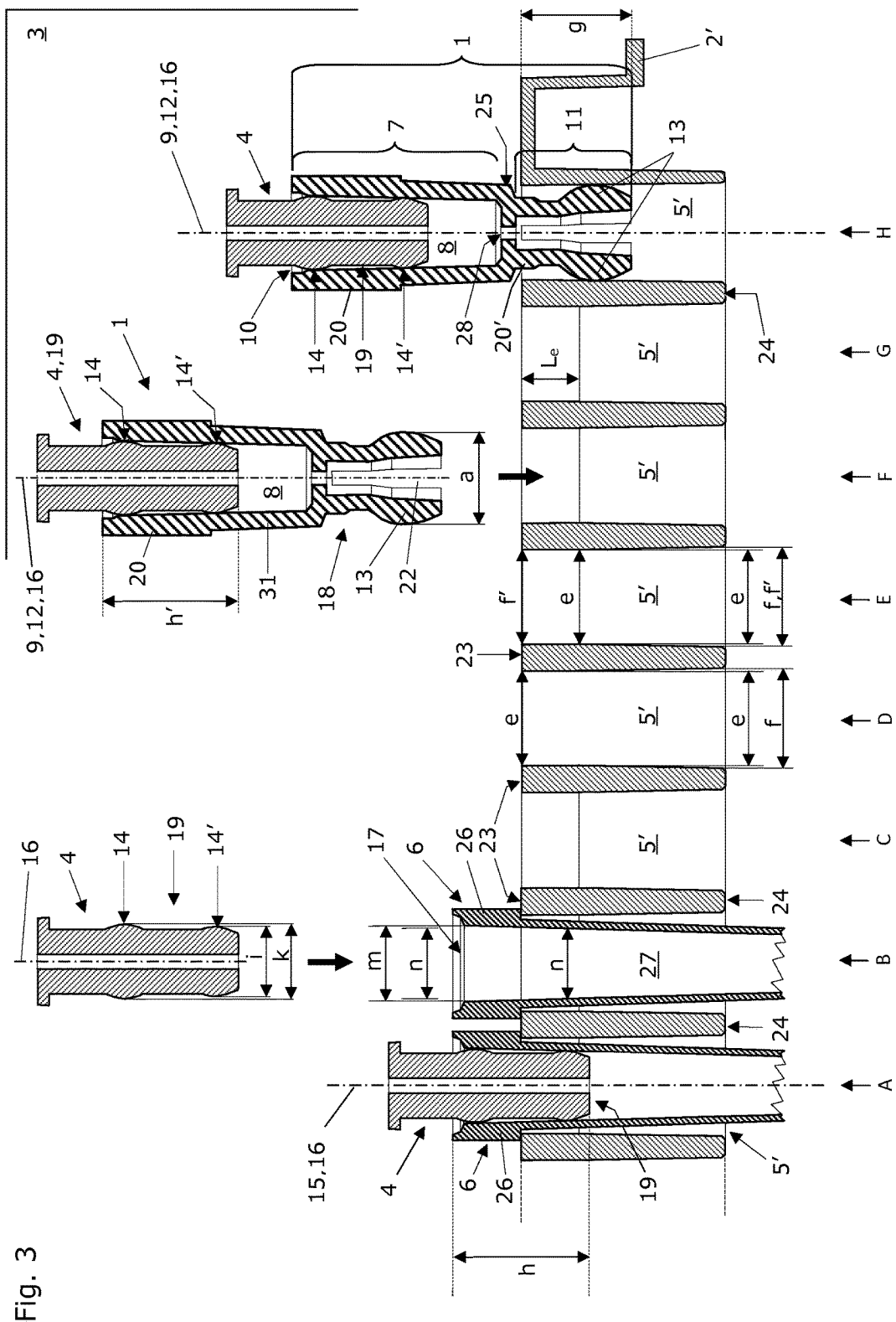
Figure 4:
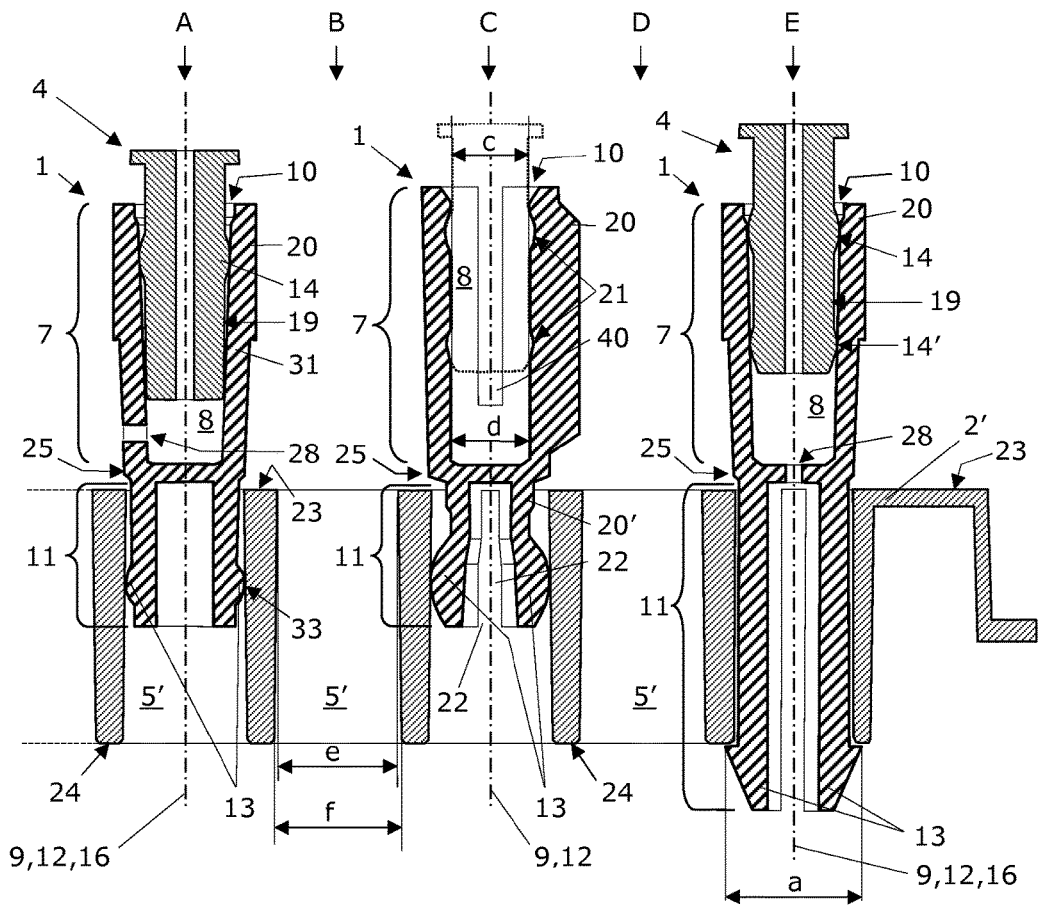
Figure 5:
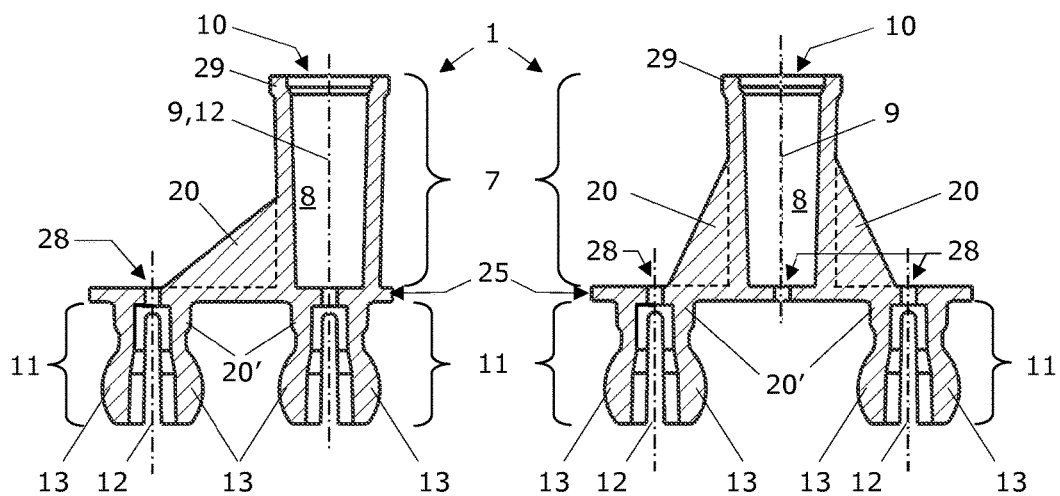
Figures 6A, 6B:
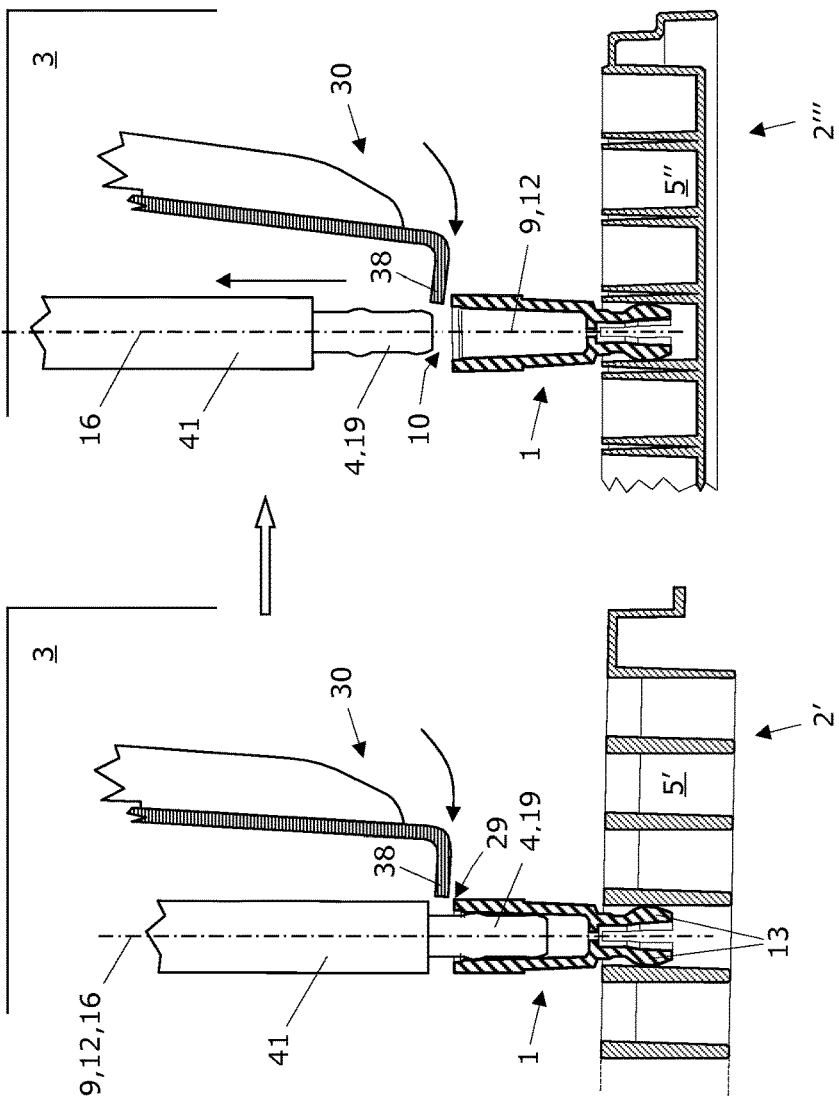
Figure 7A:
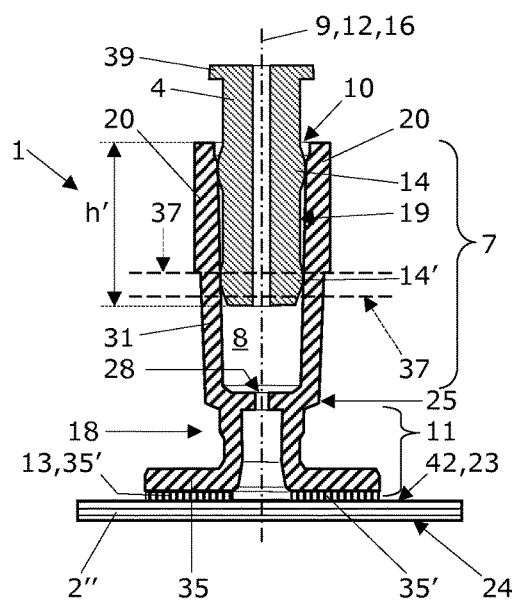
Figure 7B:
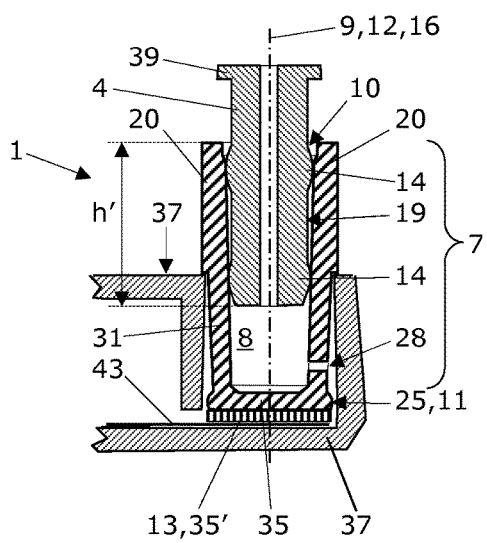
Figure 8A:
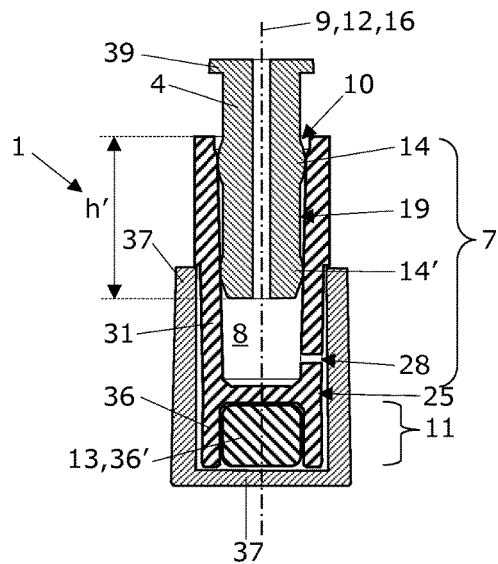
Figure 8B:
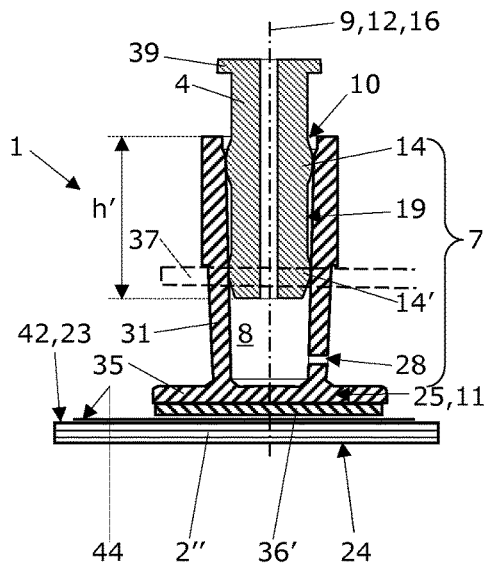

The present invention will be explained in greater detail hereafter by means of drawings which are appended to this application. The figures in these drawings disclose preferred embodiments of the invention in this case, without restricting the scope thereof, since the individual elements thereof can be combined with one another as needed. There is shown in:

FIGS. 1A and 1B are overview drawings of a transport tool according to a preferred embodiment, wherein:
FIG. 1A shows a schematic front view, and
FIG. 1B shows a vertical cross section;
FIG. 2 vertical cross-sectional drawings in each case through a transport tool according to the present invention, through the receptacle end of a pipette tip from the prior art, and through a disposable pipette tip from the prior art;
FIG. 3 a vertical cross section through a pipette tip carrier having:
two plugged-in disposable pipette tips from the prior art, wherein the receptacle end of a pipette is already plugged in a friction-locked manner into one of these freely mounted pipette tips and a pipette is indicated for the second pipette tip, which is positioned above this pipette tip to be plugged in;
a transport tool, which is plugged in a friction-locked manner onto the receptacle end of a pipette and is positioned to be plugged into a free storage opening of the pipette tip carrier above this storage opening; and
a transport tool which is already plugged by means of a pipette into a free storage opening of the pipette tip carrier;
FIG. 4 a vertical cross section through a pipette tip carrier having three plugged-in transport tools, wherein each transport tool is shown with different embodiments of its essential elements in each case;
FIG. 5 vertical cross-sectional drawings through two transport tools having two article holders in each case in alternative embodiments;
FIGS. 6A and 6B are overview drawings of the principle of discarding a transport tool, which is plugged onto a pipette, having plugged-on a pipette tip carrier or a disposable pipette tip, using a discarding mechanism of the pipetting system, wherein:
FIG. 6A sketches the principle of discarding a transport tool, which is plugged onto a pipette, having pipette tip carrier or microplate by means of the discarding mechanism in two steps; and
FIG. 6B similarly thereto, sketches a pipette having plugged-on disposable pipette tip and discarding mechanism;
FIGS. 7A and 7B are vertical sections through two transport tools, each having an article holder implemented to form an adhesive bond, wherein:
FIG. 7A shows a first variant having a ring-shaped adhesive means; and
FIG. 7B shows a second variant having a circular or square adhesive means;
FIGS. 8A and 8B are vertical sections through two transport tools, each having an article holder implemented to form a magnetic connection, wherein:
FIG. 8A shows a first variant having an integrated permanent magnet; and FIG. 8B shows a second variant having a glued-on strip magnet.

DETAILED DESCRIPTION OF THE PRESENT INVENTION

FIG. 1A shows a simplified, schematic front view of a transport tool according to the present invention in a particularly preferred embodiment. This transport tool 1 is an oblong hollow body and is implemented so that it can be plugged onto a receptacle end 19 of a pipette 4 of a pipetting system 3 with its first end, which is implemented as a plug-in sleeve, and additionally can be plugged into an opening 5 of a laboratory article, for example, into a storage opening 5' of a pipette tip carrier 2' provided for disposable pipette tips 6, with its second end, which is implemented as an article holder 11. The transport tool additionally comprises a connecting part 25, which connects the plug-in sleeve 7 to the article holder 11. The plug-in sleeve 7 comprises a sleeve axis 9, which corresponds to its longitudinal axis. The article holder 11 comprises a holding axis 12, which defines the axis along which a support connection (a plug connection here) is formed between the article holder 11 of the transport tool 2 and a storage opening 5' of the pipette tip carrier 2' (cf. also FIGS. 3, 4, 6A and 6B).

To plug the transport tool 1 onto the receptacle end 19 of a pipette 4 using its plug-in sleeve 7, this plug-in sleeve 7 comprises a receptacle opening 10, which opens into an interior 8. The interior 8 of the plug-in sleeve 7 is implemented in this case so that the transport tool 1 can form a releasable plug connection with a plugged-in pipette 4 by means of the plug-in sleeve 7. For this purpose, a pipette 4 of a pipetting system 3 is inserted with its receptacle end 19 through the receptacle opening 10 into the interior 8 up to a predefined plunging depth h' (see FIGS. 2-4). If the interior 8 of the plug-in sleeve 7 is correctly adapted to the external dimensions of the receptacle end 19 of the pipette 4, the releasable plug connection is formed between the plug-in sleeve 7 and the pipette 4 as soon as the predefined plunging depth is reached (see also FIGS. 3 and 4). The embodiment of the interior 8 of the plug-in sleeve is selected in this case so that the transport tool 1 can be plugged onto the same pipette 4 instead of a disposable pipette tip 6 and can also be discarded again, i.e., the same device settings of the pipetting system 3 can thus be used for receiving and discarding the transport tool 1 as were programmed and can be used for receiving and discarding a disposable pipette tip. It is thus preferable that, for example, a specific pipette 4 is insertable by the same plunging depth h (see FIGS. 2-4) and with the same force into a specific disposable pipette tip 6 as into the transport tool 1 according to the invention, which essentially forms an equivalent releasable plug connection with the receptacle end 19 of the pipette 4 in this case.

The term "receptacle end 19 of a pipette 4" is understood in conjunction with the present invention as the end region of a pipette 4 of a pipetting system 3, which is provided to form the releasable plug connection with a disposable pipette tip 6 or with a transport tool 1 according to the present invention.

The term "releasable plug connection" is also understood in conjunction with the present invention as a preferably sealed connection between the receptacle end 19 of a pipette 4 and a counterpart adapted thereto (for example, a disposable pipette tip 6 or a transport tool 1 according to the invention). Such a "releasable plug connection" results when the two parts are moved into a defined position in relation to one another. In addition to a sealing function, such a releasable plug connection, which is known with respect to disposable pipette tips per se from the prior art, additionally has a holding function. Thanks to this holding function, in this case a plugged-on pipette tip continues to be held to form a seal on the receptacle end 19 of a pipette tip 4, even if the pipette 4 is moved back-and-forth by means of a robot mechanism between various X/Y/Z positions on the work area of the pipetting system 3.

It could actually be established in the case of a transport tool 1 which is thus embodied that it can be received and discarded like a known disposable pipette tip 6 for a specific pipette type of a specific pipetting device 3, and that the sealing and holding force of the releasable plug connection formed is sufficient to also lift up such a transport tool 1 plus the additional weight of a pipette tip carrier 2' suspended thereon, as is also known from the prior art, by means of this pipette tip 4 and reposition it on the work area.

For the function of the transport tool 1 according to the invention per se—in contrast to the disposable pipette tip 6—in this case the sealing action of the releasable plug connection is not decisive. However, it is also inherently provided, since the transport tool 1 is to be able to be received and discarded similarly to and instead of a disposable pipette tip 6 for the same pipette 4, i.e., the same device settings are usable for receiving and discarding.

In the scope of the present invention, such a plug connection between the transport tool 1 according to the invention and the receptacle end 19 of a pipette 4 is a releasable support connection, if these two parts are separable from one another again by means of a discarding mechanism of the pipetting system 3. The force which must be applied to discard a pipette tip 6 or a transport tool 1 corresponds to approximately 205 g to 400 g. Experience has shown that a transport tool 1 according to the invention is therefore capable of receiving and transporting laboratory articles having a total weight of up to 400 g, wherein receiving and transporting laboratory articles having a total weight of at most 205 g to 400 g is especially preferred.

As is known from the prior art with respect to disposable pipette tips 6, such a releasable plug connection can be form-fitted, friction-locked, or a combination of form fit and friction lock. In particular to improve a friction-locked connection, it can be provided in this case that an additional surface which increases the friction is provided on the corresponding region of the transport tool 1. This applies both to a surface of the interior 8 of the plug-in sleeve 7, and also to an outer side 32 of the at least one holding means 13 of the article holder 11.

With a plugged-on transport tool 1 according to the invention, a pipette 4 can then be used to receive, for example, an empty pipette tip carrier 2' and reposition it on the work area of the pipetting system 3. For this purpose, the transport tool 1 plugged onto the pipette 4 is additionally plugged into a free storage opening 5' of a pipette tip carrier 2', so that it couples this pipette tip carrier 2' onto the pipette 4. Alternatively, the transport tool 1 can be coupled onto another laboratory article 2, which has an opening 5 dimensioned similarly in the dimensions to the storage openings 5' or has an attached cylinder having similar internal dimensions (not shown). It is also conceivable that the transport tool 1 is implemented for coupling with other laboratory articles 2, for example, on microplates 2''' (the wells 5'' of which are used as the opening 5 for plugging in an article holder 11), covers of microplates, or other containers, if its article holder 11 was adapted accordingly in its shape or dimensions.

To plug the transport tool 1 into a free storage opening 5' of a pipette tip carrier 2' with its article holder 11, it comprises at least one holding means 13. This holding means 13 is implemented so that, when the transport tool 1 has been inserted sufficiently far into the free storage opening 5, it forms a plug connection with this storage opening 5.

The term "plug connection" is understood—in conjunction with the support connection between the transport tool 1 according to the invention and a pipette tip carrier 2'—as a plug connection, which above all assumes a holding function between the transport tool 1 and this laboratory article 2. It is to be ensured above all in this case that when the transport tool 1 is both plugged onto a pipette 4 and also plugged into a free storage opening 5' of a pipette tip carrier 2', the connection between tool 1 and carrier 2' and between tool 1 and pipette 4 does not disengage again solely due to the weight of the carrier 2' as soon as the pipette 4 lifts and repositions the transport tool 1 and the pipette tip carrier 2'.

In conjunction with the present invention, this plug connection between the at least one holding means 13 and the pipette tip carrier 2' can be provided, for example, by friction between at least one partial surface of the outer side 32 of the holding means 13 and at least one partial surface of the inner side of the free storage opening 5 of the pipette tip carrier 2'. As already mentioned, a friction-increasing surface can be provided for this purpose on the outer side 32 of the holding means 13. Alternatively, two holding means can also be used to form this plug connection, which form a finger-shaped snap hook, which completely penetrates the storage opening 5 and is then applied to the bottom side 24 of the pipette tip carrier 2' (see FIG. 4, position E). It thus also applies for this plug connection that, as is known from the prior art, it can be friction-locked or form-fitted or a combination of friction lock and form fit.

Alternatively to holding solely by mechanical friction or a snap closure, an adhesive bond, for example, according to FIGS. 7A and 7B, can also be provided. In this case, the holding means 12 of the article holder 11 has a flat holding plate 35, which protrudes downward, pointing away from the plug-in sleeve 7 of the transport tool 1, at least approximately perpendicularly to the longitudinal axis 16 of the pipette 4 or the holding axis 12, and which is provided with an adhesive means 35'. This adhesive means 35' is preferably selected from a group of adhesives which includes dry adhesives and pressure-sensitive adhesives, wherein the use of such adhesives is known per se to a person skilled in the art from other fields of technology (for example, from building construction or model building). As shown in FIG. 7A, the holding plate 35 can be set back by means of a neck part 18 from the plug-in sleeve 7 and the connecting part 25. Alternatively thereto, as shown in FIG. 7B, the holding plate 35 can be implemented as a radial extension of the connecting part 25. To avoid the occurrence of overpressure in the interior 8 of the plug-in sleeve 7 during the plugging in of the receptacle end 19 of the pipette 4 or a partial vacuum in the interior 8 of the plug-in sleeve 7 during the discarding of the transport tool 1, it preferably comprises a ventilation hole 28, the arrangement of which is preferably oriented, for example, according to the implementation of the holding plate 35 (cf. FIGS. 7A and 7B). In order that a load-bearing adhesive bond can result between the transport tool 1 and a laboratory article 2 to be transported, the laboratory article 2 preferably has a clean, flat contact surface, to which the holding plate 35 is aligned in parallel and which is aligned at least approximately perpendicularly to the holding axis 12 of the article holder 11.

Preferably, the holding axis 12 of the article holder 11 is aligned vertically and that of the holding plate 35 is aligned horizontally.

Also alternatively to the holding solely by mechanical friction or a snap closure, a magnetic connection can also be provided, for example, according to FIGS. 8A and 8B. In this case, the holding means 13 of the article holder 11 has a flat holding plate 35, which protrudes downward, points away from the plug-in sleeve 7 of the transport tool 1, and is at least approximately perpendicular to the longitudinal axis 16 of the pipette 4 or the holding axis 12 (cf. FIG. 8B) or a holding sleeve 36, which is provided with a magnetic means 36'. This magnetic means 36' is preferably a permanent magnet, for example, in the form of a cylindrical magnet body (cf. FIG. 8A), which is glued or fastened in the holding sleeve 36 of the transport tool 1. Alternatively, a flatly acting magnetic strip is preferred as the magnetic means 36', which is fastened on the preferably horizontally aligned holding plate 35 (cf. FIG. 8B). In order that a load-bearing magnetic connection can result between the transport tool 1 and a laboratory article 2 to be transported, the laboratory article 2 preferably has a clean, flat contact surface, which is aligned at least approximately perpendicularly to the holding axis 12 of the article holder 11. A magnetizable film 44 or a magnetic strip is preferably fastened on this contact surface of the laboratory article 2, with which the magnetic means 36' of the transport tool 1 can have a magnetic interaction and thus the transport tool 1 can lift the laboratory article 2.

To prevent the occurrence of an overpressure in the interior 8 of the plug-in sleeve 7 during the plugging in of the receptacle end 19 of the pipette 4 or a partial vacuum in the interior 8 of the plug-in sleeve 7 during the discarding of the transport tool 1, it preferably comprises a ventilation hole 28, the arrangement of which is preferably oriented, for example, according to the implementation and arrangement of the holding plate 35 (cf. FIGS. 7A, 7B, 8A, and 8B).

In contrast to the releasable plug connection, which is formed between the transport tool 1 and the receptacle end 19 of a pipette 4, however, the plug connection between the transport tool 1 and a laboratory article 2, for example, a pipette tip carrier 2', does not have to be releasable. The important function of this plug connection is the holding function or support function, as mentioned above. Whether or not this plug connection is to be releasable is dependent above all on whether or not the transport tool 1 is to be releasable again from the laboratory article 2, for example, for reuse. Such an ability to release the support connection between transport tool 1 and laboratory article 2 is typically provided in the case of a plug connection as shown in FIGS. 3, 4 (positions C and E), 5, and 6. An ability to release this support connection is also provided in the case of magnetic connections, as shown in FIGS. 8A and 8B. In the case of support connections between transport tool 1 and laboratory article 2, which are based on an adhesive bond (cf. FIGS. 7 A and 7B), an ability to release cannot normally be presumed.

Various possible embodiments with respect to the sealing function, the holding function or support function, and the ability to release are known per se to a person skilled in the art, so that these are not to be discussed further.

The transport tool 1 shown in FIGS. 1A and 1B comprises, in the particularly preferred embodiment, an article holder 11 having a holding means 13. Using this holding means 13, the transport tool 1 can be plugged in a friction-locked manner into a free storage opening 5 of a pipette tip carrier 2', for example. In this particularly preferred embodiment, the one holding means 13 is implemented as essentially spherical. Alternatively, the holding means 13 can also be implemented as ellipsoidal or ovoid, for example. It is particularly preferable here for the holding means 13 to comprise at least one slot 22. The slot 22 extends, originating from the end of the article holder 11 opposite to the connecting part 25, in the direction of the connecting part 25 and goes beyond the greatest transverse extension of the article holder 11 with respect to its holding axis 12. This slot 22 provides the holding means 13 with a spring function, so that the transport tool 1 is implemented so it can be plugged in a friction-locked manner with its article holder 11 under elastic deformation of the holding means 13 into a storage opening 5 of the pipette tip carrier 2'.

In the embodiment shown in FIGS. 1A and 1B, the essentially spherical holding means 13 is connected via a narrow neck part 18 of the article holder 11 to the connecting part 25. The at least one slot 22 preferably extends over the greatest transverse extension of the article holder 11 with respect to its holding axis 12 up into the narrow neck part 18. This combination of slotted, narrow neck part 18 and also slotted, essentially spherical holding means 13 increases the spring action of the holding means and therefore makes it easier to plug the transport tool 1 into the storage opening 5. An increased spring force improves the holding of the spherical holding means 13 in the storage opening 5 and the transportability of the pipette tip holder 2 using the transport tool 1 and the pipette 4 of the pipetting system 3.

In a particularly preferred embodiment, the slot 22 extends along the direction of the holding axis 12 of the article holder 11. Alternatively, the slot 22 can also extend at an angle to the holding axis 12 of the article holder 11. In addition, the slot 22 can extend in a straight line or alternatively in a line deviating from a straight line. However, the slot 22 particularly preferably extends along a straight line and along the direction of the holding axis 12 of the article holder 11.

If the at least one holding means 13 of the article holder 11 of the transport tool 1 is implemented as essentially spherical as in FIGS. 1A and 1B and comprises the slot 22 as described above, the releasable plug connection formed is essentially based on a releasable friction lock. The friction lock is produced in this case between the region of the outer side 32 of the holding ball 13 having the greatest transverse extension with respect to the holding axis 12 and the inner surface of the free storage opening 5 of the pipette tip carrier 2'. Further details on the insertion and holding of the transport tool in a free storage opening 5 are discussed in conjunction with FIGS. 3 and 4.

The transport tool 1 additionally comprises a connecting part 25, which connects the article holder 11 to the plug-in sleeve 7 on its end opposite to the receptacle opening 10. Therefore, the transport tool 1 can be plugged with one side onto the pipette 4 of a pipetting system, and can be plugged with its other side into a free storage opening 5 of a pipette tip carrier 2'. An already provided pipette 4 of the pipetting system 3 can thus be used, for example, to lift an empty pipette tip carrier 2' from its present position, transport it to another position, for example, a disposal station, and then discard this empty pipette tip carrier 2' there.

This usage of the pipette 4 already present on the pipetting device can be performed without an additional gripper arm being necessary, and without further modifications being necessary on the pipetting system 3. This is possible because the transport tool 1 is structured and dimensioned so that—using the same settings on the device —it can simply be plugged onto the pipette 4 instead of a disposable pipette tip 6 and additionally thus engages in a free storage opening 5 of a pipette tip carrier 2' so that it also lifts the pipette tip carrier 2' accordingly upon lifting of the pipette 4. The lifted pipette tip carrier 2' can then be moved to the desired position by the corresponding movement of the pipette 4. The transport tool 1 together with the plugged-on pipette tip carrier 2' (cf. FIG. 6A) or the plugged-on microplate 2''' (cf. FIG. 6B) can then be discarded at this desired position using the discarding mechanism 30, which is also already provided, with application of the same settings as for discarding a disposable pipette tip 6.

Disposable pipette tips 6 are known to a person skilled in the art from the prior art. In this case, disposable pipette tips 6 are understood as those pipette tips which are generally used for only one pipetting operation or for as few pipetting operations as possible and are disposed of again after use. Such disposable pipette tips 6 can be plugged on in this case, as mentioned, in a friction-locked or form-fitted manner, or in a combination of friction lock and form fit, but always to form a seal, onto a pipette 4.

The transport tool 1 shown in FIGS. 1A and 1B additionally comprises, on its end having the receptacle opening 10, a collar 29. This collar 29 preferably extends completely around the outer side of the plug-in sleeve 7 at its uppermost edge. It provides an enlarged surface on the top side of the plug-in sleeve 7, to which a discarding mechanism 30 of the pipetting system 3 can be applied particularly well. The use of a collar 29 is known per se to a person skilled in the art from the prior art in the design of pipette tips 6. The attachment of such a collar in the case of pipette tips 6 is preferred to provide an enlarged top edge, so that the application of a discarding mechanism is simplified, and to provide the pipette tip with additional stability when it is received with force, for example, on the receptacle end 19 of a pipette 4, for example. The attachment of a collar 29 in the case of disposable pipette tips 6 and in the case of a transport tool 1 according to the invention is optional and is dependent on the requirements for the pipette tip 6 or the transport tool 1. The decision about whether a collar 29 should be attached to the plug-in sleeve 7 of the transport tool 1, and also the selection of the thickness and height of the collar 29 is within the knowledge of a person skilled in the art and is additionally oriented to the embodiment of the discarding mechanism 30 of the pipetting system 3 to be used. In the particularly preferred embodiment according to FIGS. 1A and 1B, the transport tool 1 comprises a collar 29.

The use of at least two reinforcement struts 20 on the outer side 34 of the plug-in sleeve 7 is also optional, but is particularly preferred. Each reinforcement strut 20 preferably extends in the direction of the sleeve axis 9. In addition, further reinforcement struts 20' can be provided on the transport tool 1, for example, if a narrow, partially slotted neck part 18 is provided, as in the particularly preferred embodiment shown here. The use of reinforcement struts 20, 20' is also known per se to a person skilled in the art from the prior art in the design of disposable pipette tips 6. The attachment of reinforcement struts is preferred in the case of disposable pipette tips 6 to provide them with increased stability in their top region, for example. This is particularly advantageous to prevent or at least minimize possible deformations of the pipette tip 6 due to the insertion of the receptacle end 19 of the pipette tip 4 for the sealed plugging in. Such a deformation could actually impair the sealing effect between the interior 27 of the disposable pipette tip 6 and the outer side of the receptacle end 19 of the pipette 4, which in turn could result in impairment of the precision of the aspiration and dispensing operation. In addition, with the smallest possible deformation due to the application of a discarding mechanism 30, the required settings in the pipetting system 3, for example, the maximum required force for releasing a specific disposable pipette tip 6 from the pipette 4, can be standardized more easily.

In addition, reinforcement struts 26 are used in disposable pipette tips 6 to hold them in a storage opening 5 of a pipette tip carrier 2' or to support the disposable pipette tips 6 on the surface of the pipette tip carrier 2'. For this purpose, the pipette tip 6 should comprise at least three reinforcement struts 26, which, when the pipette tip 6 is stored in the pipette tip carrier 2', are applied to its surface. At least three such reinforcement struts are necessary so that the tip can stand without tilting in the pipette tip carrier 2'.

Reinforcement struts 20, 20' can also be used accordingly in the transport tool according to the invention. The selection of the number, thickness, shape, and length of reinforcement struts 20 and the arrangement thereof on the transport tool 1 according to the invention is within the knowledge of a person skilled in the art in this case. However, the plug-in sleeve 7 particularly preferably comprises at least three reinforcement struts 20 on its outer side 34, which extend in the direction of the sleeve axis 9, and which are distributed at least approximately uniformly around the circumference of the plug-in sleeve 7. The transport tool 1 strikes with the bottom side of these reinforcement struts 20 on a surface of a tool carrier 37 for storing and providing transport tools 1.

FIG. 1B shows the transport tool 1 according to the particularly preferred embodiment in a vertical cross-sectional drawing, as it is mounted in a special tool carrier 37. The tool carrier 37 also comprises—similarly to a pipette tip carrier 2'—storage openings, in each of which a transport tool 1 is stored and provided for use. It is well recognizable here how the transport tool 1 applies the bottom sides of the reinforcement struts 20 to a top side of the tool carrier 37 and is thus held "standing" thereon. These are preferably the only contact points between transport tool 1 and its tool carrier 37: The storage opening of the tool carrier, in particular its internal diameter r, is adapted to the dimensions of the transport tool 1 so that its inner surface is not contacted thereby during the storage of a transport tool 1, so that the transport tool 1 can be lifted out of the tool carrier 37 with as little resistance as possible by a pipette 4.

The internal diameter r of the storage opening in the tool carrier 37 for the transport tool 1 is adapted to the actual external diameter a of the article holder 11 or its holding means 13. Exemplary dimensions are:

a: 7.18 mm (=external diameter of the spherical holding means 13);

r: 7.6+0.05 mm (=internal diameter of the storage opening).

The design of the tool holder 37 for storing the transport tool 1 is not relevant for the function of the transport tool 1 itself. However, it can be provided, for example, that the tool holder 37 is positionable at those positions on the work area of a pipetting system 3 which were originally provided, for example, for a container for providing larger liquid volumes (for example, 25-150 ml). The storage of the transport tool 1 or a larger number of transport tools 1 can thus also be performed in a space-saving manner. As an example, it is furthermore mentioned here that such a tool holder 37 could be implemented so that it can accommodate 16 transport tools 1. These 16 transport tools 1 are sufficient, for example, to process, i.e., reposition, four stacks each having five pipette tip carriers 2' (presuming that in each case the lowermost pipette tip carrier 2' always remains in position).

In addition, it can be inferred from FIG. 1B that the transport tool 1 is implemented as a hollow body; the implementation of the interior 8 of the plug-in sleeve 7 can thus be inferred well from this cross-sectional drawing. In this particularly preferred embodiment, the interior 8 of the plug-in sleeve is implemented as conically tapering toward the connecting part 25. This embodiment is preferred if the transport tool 1 is to be able to be plugged onto a conically tapering receptacle end 19 of a pipette 4. Actually, such conically tapering receptacle ends 19 are a frequently used form of the pipette end, since, in combination with the easily producible disposable pipette tips having internal cone, it can easily and reliably form a releasable, friction-locked, and sealed plug connection. Such conically tapering receptacle ends 19 of pipettes 4 are also known in shortened form as "receptacle cones" in the prior art and are described in greater detail in conjunction with FIG. 2.

Alternatively, it can be provided that the interior 8 of the plug-in sleeve 7 is implemented as cylindrical; this is preferred, for example, when the receptacle end 19 of the pipette 4 is also implemented as cylindrical and a form-fitted, releasable plug connection is provided (see also FIG. 4 and the corresponding discussion in this regard).

However, it is particularly preferable for the interior 8 of the plug-in sleeve 7 to be implemented as conically tapering, wherein the receptacle opening 10 for the pipette 4 is arranged on the wider end and the connecting part 25 is arranged on the narrower end of the interior 8. The plug-in sleeve 7 can thus be plugged in a friction-locked manner onto the receptacle end 19 of the pipette 4, if this is also implemented as conically tapering, for example, if the receptacle end 19 has a ring-shaped protrusion 14 spaced apart from the end of the pipette (cf. FIGS. 2 and 3).

As mentioned above, the interior 8 of the plug-in sleeve 7 is adapted to the receptacle end 19 of a pipette 4 so that the transport tool 1 can be received, held, and released like a disposable pipette tip 6 of the same pipette type. It is known per se to a person skilled in the art that the interior 27 of such disposable pipette tips 6 is embodied such that when the pipette 4 is plugged in, not only is the disposable pipette tip 6 securely held on the pipette 4, but rather additionally a seal is formed between pipette 7 and pipette tip 6. Exact aspiration and dispensing by the pipetting device 3 can only be ensured when the pipette 4 closes the interior 27 of the disposable pipette tip 6 to form a seal. For the function as a coupling between a pipette 4 and a transport tool 1, the sealing closure of the interior by the pipette 4 is not necessary per se. However, it results indirectly from the requirements that the transport tool 1 can be held and released again in the most similar possible manner on the pipette 4 as a corresponding pipette tip.

The positions of the sleeve axis 9 of the plug-in sleeve 7 and the holding axis 12 of the article holder 11 can additionally be inferred from FIG. 1B. In this particularly preferred embodiment which is shown, the connecting part 25 connects the article holder 11 to the plug-in sleeve 7 so that the holding axis 12 of the article holder 11 and the sleeve axis 9 of the plug-in sleeve 7 are arranged coaxially to one another. Alternatively thereto, however, it can be provided that the holding axis 12 and the sleeve axis 9 are arranged axially parallel to one another. This is preferable if the transport tool 1 has more than one article holder 11—for example, as shown in FIG. 5, two article holders 11 arranged parallel to one another. The embodiment of a transport tool 1 having two article holders 11 is particularly preferred if, for example, the load which can be lifted by the transport tool 1 is to be increased or the friction lock between the article holder 11 and the openings 5 of a specific laboratory article 2 is to be reduced.

It can also be seen well in FIG. 1B that in the particularly preferred embodiment of the transport tool 1, a ventilation hole 28 is provided. This is to enable a pressure equalization in the interior 8 of the plug-in sleeve 7 if, to plug the transport tool 1 onto the pipette 4, the receptacle end 19 of the pipette 4 is to be inserted into the interior 8 of the plug-in sleeve 7. In the particularly preferred embodiment shown in FIGS. 1A and 1B, the connecting part 25 comprises the at least one ventilation hole 28. A continuous interior thus results, which extends originating from the receptacle opening 10 up to the end of the article holder 11 or its holding means 13.

Alternatively, it can be provided that the connecting part 25 does not provide the ventilation hole 28 (or a plurality thereof), but rather, for example, a side wall 31 of the plug-in sleeve 7, wherein each ventilation hole 28 completely penetrates this side wall 31 to enable a pressure equalization (see also FIG. 4, position A and FIGS. 7B, 8A, and 8B in this regard). Instead of a ventilation hole 28 (or additionally) a slot 42 which completely penetrates the wall can also be provided, which extends in the direction of the sleeve axis 9 and is not only used for ventilation, but rather also makes it easier to insert the receptacle end 19 of the pipette 4 into the interior 8 of the plug-in sleeve 7, for example, if the releasable plug connection is to be form-fitted (see also FIG. 4, position C).

In FIG. 2, a transport tool 1 according to the invention, a pipette 4, which is known per se from the prior art, with its receptacle end 19, and a disposable pipette tip 6, which is also known per se from the prior art, are each shown in a cross-sectional drawing adjacent to one another. In this case, the relevant relationships between a transport tool 1 according to the invention, a selected receptacle end 19 of a pipette 4 and a disposable pipette tip 6 are illustrated, so that the transport tool 1 can be plugged onto a pipette 4 (and can be discarded therefrom) instead of a known disposable pipette tip 6.

In principle, it is preferable for the dimensions of the receptacle end 19 of the pipette 4 to determine the dimensions of the interior 8 of the plug-in sleeve 7, i.e., for the pipetting device to specify the implementation of the transport tool 1. This is a procedure known per se from the prior art for producers of disposable pipette tips 6: Pipetting devices of various producers can also have variously shaped and differently dimensioned receptacle ends 19 of the pipettes 4 used, so that corresponding disposable pipette tips 6 having different internal dimensions are required for the various pipettes 4, in order that a pipette tip can form a sealing and nonetheless releasable plug connection with the corresponding pipette 4 of the device. This approach has proven itself, because thus the technically complicated part "pipette" does not have to be replaced for various pipette tips. Instead, the significantly more cost-effective mass-produced article (the disposable pipette tip 6 or the transport tool 1) can be adapted to the pipette 4 during the production thereof.

A pipette 4 having a conical receptacle end 19 is shown in the middle of FIG. 2. receptacle end 19 is thus implemented here as conically tapering toward the lower end of the pipette 4. The use of a receptacle cone is particularly preferable if, for example, a friction-locked, releasable plug connection is to be implemented between the pipette 4 and a disposable pipette tip 6 or a transport tool 1. The conicity of the receptacle end 19 shown in FIG. 2 is achieved in this case in that it has two circumferential ring-shaped protrusions 14,14', which are spaced apart from one another and from the end of the pipette 4. In this case, the largest external diameter k of the upper protrusion 14 is larger than the largest external diameter i of the lower protrusion 14', which is closer to the end of the pipette 4. The receptacle end 19 is thus wider in the region of the upper ring-shaped protrusion 14 than in the region of the lower ring-shaped protrusion 14'. Therefore, the external surfaces thereof and the distance $L_{14\text{-}14'}$ thereof to one another define the degree of the conicity. These ring-shaped, circumferential protrusions 14,14' are positioned in this case at a distance to the end of the pipette 4 so that both can still plunge at their largest external diameters i, k into the disposable pipette tip 6 or into the transport tool 1, respectively. Upon reaching a defined plunging depth h,h', the circumferential protrusions 14,14' contact the inner wall of the disposable pipette tip 6 or the interior 8 of the plug-in sleeve 7 of the transport tool 1 and form the friction lock therein with the disposable pipette tip 6 or the transport tool 1.

Alternatively, the conicity of the receptacle end 19 can also be achieved in that only a single ring-shaped protrusion 14, which is spaced apart from the end of the pipette 4, is provided, so that the largest external diameter k of this ring-shaped protrusion is larger than any external diameter q of the receptacle end 19 in the direction of the end of the pipette 4 (see FIG. 4, position A).

The plunging depth h for a specific combination of pipette 4 and disposable pipette tip 6 and also the plunging depth h' for a corresponding combination of pipette 4 and transport tool 1 is predetermined in each case. If the respective plunging depth h,h' is achieved, the pipette tip 6 or the transport tool 1 is thus seated plugged on releasably on the receptacle end 19 of the pipette 4. The insertion of the receptacle end 19 of a pipette 4 into the interior 27 of the pipette tip 6 or into the interior 8 of the transport tool 1, respectively, can be performed automatically in the common automatic pipetting machines. For this purpose, the force to be applied is ascertained beforehand, which is required to push the pipette 4 with its receptacle end 19 into the disposable pipette tip 6 or into the transport tool 1 until the desired plug connection is formed.

For example, such a conically tapering receptacle end 19 of a pipette 4 can have the following dimensions, which are identified accordingly in FIG. 2:

h,h': 11.1 mm (=plunging depth into an adapted disposable pipette tip 6/into an adapted transport tool 1);
i: 5.13 mm (+0.01 mm/−0.03 mm; =largest external diameter of the lower, ring-shaped protrusion 14');
k: 5.45 mm (+0.01 mm/−0.03 mm; =largest external diameter of the upper, ring-shaped protrusion 14);
$L_{14\text{-}14'}$: 6.5 mm (+/−0.02 mm; =length of the spacing between i and k);
$L_{35}$: 14 mm (=total length of the receptacle end 19 between the end of the pipette 4 and an upper edge 39);
q: 4.7 mm (=external diameter of the pipette in the region of the receptacle end 19).

Receptacle ends 19 of a pipette 4 of a pipetting system 3, which are not implemented as conical but rather essentially cylindrical, are also known. In this case, the interior 8 of the plug-in sleeve 7 of the transport tool 1 according to the invention is also implemented as complementary, i.e., cylindrical. To enable the formation of a releasable plug connection, however, additional structures have to be provided here on the receptacle end 19 of the pipette 4; complementary structures also have to be provided accordingly in the interior 8 of the plug-in sleeve 7 (see FIG. 4, position C).

If a pipette 4 having receptacle end 19 or receptacle cone 19 is thus used—to implement the friction-locked, releasable plug connection—both the interior 27 of the disposable pipette tip 6 and also the interior 8 of the plug-in sleeve 7 of the transport tool 1 according to the invention are thus adapted to the receptacle cone 19, i.e., also implemented as conically tapering. In each case one such adapted transport tool 1 and one such disposable pipette tip 6 are shown as an example in FIG. 2 on the left side (the transport tool 1) and on the right side (the disposable pipette tip 6) of the pipette 4.

The disposable pipette tip 6 shown on the right side of FIG. 2 is adapted with its interior 27 to the receptacle cone 19 shown so that it can be automatically plugged thereon in a friction-locked and releasable manner. Such a disposable pipette tip 6 typically comprises reinforcement struts 26, as were already briefly described above —they are used, on the one hand, for reinforcing the upper collar region of the disposable pipette tip 6, to keep a deformation small during the insertion of the receptacle end or receptacle cone 19 of the pipette 4 or even to prevent it. In addition, these reinforcement struts 26 are used for loosely holding the disposable pipette tip 6 in a storage opening 5' of a pipette tip carrier 2'. In this case, the pipette tip 6 stands with the bottom side of these reinforcement struts 26 on the top side 23 of the pipette tip carrier 2', without contacting the inner wall of the storage opening 5' with its side walls. The disposable pipette tip 6 can thus be received easily and without resistance by a pipette 4 and moved out of the storage opening 5'.

The disposable pipette tip 6 therefore has, in the region of the reinforcement struts 26, a largest, first external diameter p, which is larger than an uppermost diameter f'(see FIG. 3, position E) of the storage opening 5' of the pipette tip carrier 2'. In addition, the disposable pipette tip 6 has a second external diameter o in the largest external region without reinforcement struts 26, which is smaller than the uppermost diameter r of the storage opening 5' of the pipette tip carrier 2'. The storage of the disposable pipette tip 6 in the pipette tip carrier 2' is enabled by the mutual adaptation of these external diameters o,p.

The interior 27 of the pipette tip 6 of FIG. 2 is conically tapering in the direction of its pipette tip opening in that its first internal diameter m, which is on top in the drawing, is larger than its second, lower internal diameter n. In this case, the conicity is adapted to the conicity of the external region of the receptacle end 19 of the pipette 4 so that a releasable, friction-locked, and sealing plug connection can be established, when the receptacle end 19 has been plugged up to the defined plunging depth h into the disposable pipette tip 6. The fine adaptations for this purpose are within the knowledge of a person skilled in the art and will therefore not be explained further here.

An exemplary disposable pipette tip 6 which is adapted to the receptacle end 19 of the pipette 4 shown in FIG. 2 can have the following dimensions, which are also identified accordingly in FIG. 2:

$L_6$: 58.3 mm (+/−0.2 mm; =total length of the disposable pipette tip 6);
m: 5.39 mm (+/−0.03 mm; =first, larger internal diameter of the disposable pipette tip 6);
n: 5.06 mm (+/−0.03 mm; =second, smaller diameter of the disposable pipette tip 6);
o: 6.5 mm (+/−0.05 mm; =first, largest diameter of the disposable pipette tip 6 without reinforcement struts 26);
p: 7.9 mm (+/−0.05 mm; =second, largest diameter with reinforcement struts 26).

A transport tool 1 according to the invention, which is adapted to the dimensions of the receptacle end 19 of a pipette 4 shown in the middle of FIG. 2, is shown on the left side of this pipette 4. The characteristic structure was already described in detail with reference to FIGS. 1A and 1B and therefore is not to be repeated here. Such an adapted transport tool 1 having conically tapering interior 8 for the releasable, friction-locked plugging onto a conically tapering receptacle end 19 according to the dimensions of FIG. 2 can itself have the following dimensions, which are also identified accordingly in FIG. 2:

a: 7.18 mm (+/−0.03 mm; =largest external diameter of the spherical, slotted holding means 13);
b: 7.15 mm (=smallest external diameter of the connecting part 25);
c: 5.47 mm (+/−0.03 mm; =first, larger internal diameter of the interior 8 of the plug-in sleeve 7);
d: 4.97 mm (+/−0.03 mm; =second, smaller internal diameter of the conical inner wall of the plug-in sleeve 7);
$L_7$: 15.5 mm (=length of the plug-in sleeve 7);
$L_{11}$: 8.5 mm (=length of the article holder 11);
$L_{13}$: 5.25 mm (=length of the spherical holding means 13);
$L_{25}$: 1 mm (=length of the connecting part 25).

The dimensions specified here are exemplary dimensions for a combination, which is adapted to one another, of transport tool 1 according to the invention and receptacle end 19 of a pipette 4 and for a combination, which is also adapted to one another, of disposable pipette tip 6 and the same receptacle end 19 of a pipette 4. It is in the scope of the knowledge of a person skilled in the art, after study of this application, to adapt the transport tool 1 according to the invention to the corresponding shape and dimensions of the receptacle end 19 of a pipette 4 depending on the desired connection.

For the combinations specified here of transport tool 1 according to the invention and receptacle end 19 of a pipette 4 and disposable pipette tip 6 and receptacle end 19 of a pipette 4, the following device parameters can be used: To receive this disposable pipette tip 6 and to receive this transport tool 1 on the pipette 4, a force of 24 N is typically required when used, for example, in the pipetting system 3 "Freedom EVO®" of the current applicant. Similarly thereto, a force of approximately 5 N is required to discard this plugged-on disposable pipette tip 6 and to discard this plugged-on transport tool 1 using the discarding mechanism 30 of the same pipetting system 3.

FIG. 3 shows a vertical cross section through a pipette tip carrier 2' known from the prior art. A disposable pipette tip 6 is mounted without resistance in each of the storage openings 5' of the positions A and B, in that it stands with the bottom side of its reinforcement struts 26 on the top side 23 of the pipette tip carrier 2'. A transport tool 1 is shown above the storage opening 5' of the position F, which is already plugged onto a pipette tip 4, and which is next to be plugged with its article holder 11 into this storage opening 5'. In the storage opening 5' of the position H, a transport tool 1, which is plugged therein with a pipette 4 is shown.

A horizontal partition line is indicated in each case for the storage openings 5' at the positions A-C and E-H. This partition line identifies a partition line between two injection mold halves, which were used for the production of the pipette tip carrier 2' shown here. To ensure good demolding ability, the corresponding storage opening 5' spreads apart slightly conically in each case in the direction of the top side 23 and the bottom side 24 of the pipette tip carrier 2'. The storage opening 5' therefore has a smallest internal diameter e at the height of the partition line. The transport tools 1 and the disposable pipette tips 6, which are shown in FIG. 3, correspond to those which were each shown and specified accordingly in FIG. 2. They are adapted to the dimensions of the storage openings 5' of this pipette tip carrier 2'.

The following are mentioned as examples of a correspondingly adapted storage opening 5' of a pipette tip carrier 2':

a: 7.18 mm (+/−0.05 mm; =largest external diameter of the holding means 13 of the transport tool 1);
e: 7.0 mm (=narrowest internal diameter in the region of the partition line);
f: 7.25 mm (=outer internal diameter on the bottom side 24 of the storage opening 5');
f': 7.1 mm (=outer internal diameter on the top side 23 of the storage opening 5').

In contrast, a storage opening 5' is shown in position D, which continuously spreads apart conically from the top side 23 of the pipette tip carrier 2' in the direction of its bottom side 24. Therefore, the outer, top internal diameter r is equal here to the narrowest diameter e of this storage opening 5'. Storage openings 5' which are implemented as cylindrical are also known (see also FIG. 4, position E).

A pipette 4 is already inserted in a friction-locked manner with its receptacle end 19 into the disposable pipette tip 6 in the storage opening 5' of position A, so that the pipette 4 would carry along the disposable pipette tip 6 during a corresponding upward movement. As already mentioned above, a friction lock is ensured for this combination at a preferred plunging depth h of the pipette 4 of 11.1 mm into the interior 27 of the disposable pipette tip 6. It is preferable in this case, when the pipette 4 is plugged in a friction-locked manner into the disposable pipette tip 6, for the longitudinal axis 16 of the pipette 4 and the longitudinal axis 15 of the disposable pipette tip 6 to be arranged coaxially.

For the disposable pipette tip 6 stored in position B, it is shown how a suitable pipette 4 is just moved down in the direction of the receptacle opening 17 of the pipette tip 6 in order to receive it. The relevant diameters at the receptacle end 19 of the pipette 4 and in the interior 27 of the disposable pipette tip 6 are emphasized here (diameters i and k of the pipette 4 and diameters m and n of the interior 27 of the disposable pipette tip 6). The pipette is thus also plugged in a friction-locked manner into the disposable pipette tip 6 here.

If a disposable pipette tip 6 is plugged in a friction-locked or form-fitted manner onto the receptacle end 19 of the pipette 4, the pipette 4 having plugged on disposable pipette tip 6 can automatically be moved to a defined position on the work area of the pipetting system 3, so that the desired action, for example, an aspirating or dispensing operation, can be carried out there.

A transport tool 1 according to the invention is shown above the free storage opening 5' of the position F, which is already plugged onto a pipette 4 or its receptacle end 19. Accordingly, a transport tool 1 stored in a tool carrier 37 was already received by the pipette 4 by lowering the pipette 4 and inserting the receptacle cone 19 into the plug-in sleeve 7 by a plunging depth h'. The transport tool 1 is shown, in the particularly preferred embodiment shown in FIGS. 1A, 1B and 2, having a conical plug-in sleeve interior 8, which tapers in the direction of the connecting part 25, and an article holder 11 having the essentially spherical, slotted holding means 13. The pipette 4 for this position (and for the positions A, B, and H) is also shown having the tapering receptacle end 19, implemented by two circumferential ring-shaped protrusions 14, 14' of different thicknesses. The transport tool 1 shown is therefore plugged in a releasable and friction-locked manner onto the pipette 4 when the pipette 4 is inserted by a preferred plunging depth h' into the interior 8 of the plug-in sleeve 7, wherein the sleeve axis 9 of the plug-in sleeve 7, the holding axis 12 of the article holder 11, and the longitudinal axis 16 of the pipette 4 are arranged coaxially to one another.

The plunging depths h and h' are essentially determined in this case by the dimensions of the receptacle end 19 of the pipette and of the interior 27 of the pipette tip 6, and the same pipette 4 preferably plunges by the same plunging depth h and h' to form the releasable plug connection both into the corresponding disposable pipette tip 6 and also into the plug-in sleeve 7 of the transport tool 1. The transport tool 1 in this particularly preferred embodiment is particularly suitable in this case to form a plug connection with a storage opening 5', which, as described above, spreads apart slightly conically from the partition line in the direction of the top side 23 and the bottom side 24 of the pipette tip carrier 2', so that this pipette tip carrier 2' can thus be raised with the pipette 4 by the transport tool 1 thus coupled and repositioned on the work area of the pipetting system 3 or disposed of. This is illustrated in the position H of the pipette tip carrier 2'.

The pipette 4 was lowered here with the plugged-on transport tool 1 in the direction of the free storage opening 5 in the position H. By way of the lowering, the spherical, slotted holding means 13 is guided into this storage opening 5', wherein the spherical holding means 13 is compressed by the spring function provided by the slot 22, so that it is elastically applied to the inner walls of the storage opening 5 as soon as it is pushed with its largest external diameter a into the regions of the storage openings 5' having equally large or smaller internal diameter. The spherical holding means 13 is firstly compressed more and more strongly until it passes the narrowest internal diameter e at the partition line. Since the internal diameter of the storage opening 5' becomes larger again in the direction of the bottom side 2, the spherical holding means 13 is then firstly compressed less strongly again when it is pushed further into the storage opening 5'. The transport tool 1 is actually pushed by means of the pipette 4 with its spherical holding means 13 beyond the narrowest internal diameter e into the storage opening 5', so that the spherical holding means 13 is firstly not positioned at a height having its greatest clamping action in the storage opening 5'.

For a transport tool 1 having the dimensions as are specified as examples in FIG. 2 (i.e., having a largest external diameter of the spherical holding means 13 of a=7.18 mm), a plug-in depth g of approximately 8 mm is preferred in this case if the narrowest internal diameter is e=7.0 mm and is spaced apart by a length $L_e$=4.0 mm from the top side 23 of the pipette tip carrier 2'.

The transport tool 1 is also lifted by a subsequent upward movement of the pipette 4 and it is firstly drawn upward again in the storage opening 5' until it reaches a position inside the storage opening 5' in which the friction force between spherical holding means 13 and inner wall of the storage opening 5' and the weight force of the pipette tip carrier 2' are of equal amounts. If the spherical holding means 13 is located in this position, it thus also lifts the pipette tip carrier 2' during a further upward movement of the pipette 4, and the pipette tip carrier 2' can also be moved above the work area of the pipetting system 3 and, for example, repositioned by the corresponding further movements of the pipette 4.

It can additionally be inferred from FIG. 3 at the position H that in this combination, reaching the preferred plug-in depth g of the transport tool 1 into the storage opening 5' is not restricted by the outer edges of the connecting part 25 (having the external diameter b, cf. FIG. 2). However, it can be possible to implement these outer edges so that their external diameter b is larger than the upper, outer internal diameter r of the storage opening 5', for example, to determine a maximum plunging depth for the transport tool 1 into the storage opening 5'.

FIG. 4 shows a vertical cross section through a pipette tip carrier 2' having three plugged-in transport tools 1, which occupy storage openings 5' in the positions A, C, and E of the pipette tip carrier 2'. Each transport tool 1 has in this case different embodiments of its essential elements plug-in sleeve 7, connecting part 25, and article holder 11 in each case. It is illustrated here as an example how the various embodiments of the plug-in sleeve 7, connecting part 25, and article holder 11 can be combined with one another to form a transport tool 1 individually adapted to a specific pipette 4 and a specific pipette tip carrier 2'.

A plugged-in transport tool 1 is shown in the position A of FIG. 4, in the case of which the interior 8 of the plug-in sleeve 7 is implemented as conically tapering toward the connecting part 25. This transport tool 1 is therefore particularly suitable to be plugged in a friction-locked manner onto a receptacle end 19 of a pipette 4, which is implemented as conically tapering toward its receptacle end 19. The conicity of the receptacle end 19 of the pipette 4 is determined in this case by means of the external diameter of only one circumferential, ring-shaped protrusion 14 and the external diameter of the pipette 4 at the end of its receptacle end 19. The plug-in sleeve 7 of this transport tool 1 comprises reinforcement struts 20 (the collar 29 is not shown here, cf. FIG. 1A). The plug-in sleeve 7 itself comprises at least one ventilation hole 28 here to enable a pressure equalization in the interior 8 of the plug-in sleeve 7.

The ventilation hole 28 penetrates a side wall 31 of the plug-in sleeve 7. The plug-in sleeve 7 can also comprise a plurality of ventilation holes 28, which penetrate the side wall 31 of the plug-in sleeve 7. In this transport tool 1, the connecting part 25 does not have a ventilation hole 28, although it does not have to be omitted.

The article holder 11 of the transport tool 1 shown in the position A of the pipette tip carrier 2' is implemented as an oblong hollow body. It comprises a plurality of holding means 13, which are implemented as projections 33 and which are arranged on the outer side 32 of the article holder 11. In this case, these holding means 13, which are implemented as projections 33, are implemented to form a friction-locked plug connection with the storage opening 5' of the pipette tip carrier 2'. For an improved clamping action, the article holder 11 can additionally be implemented as slotted (not shown).

The plugged-in transport tool 1 shown in the position C of FIG. 4 comprises a plug-in sleeve 7, using which the transport tool 1 can be plugged in a form-fitted manner onto a receptacle end 19 of a pipette 4. For this purpose, the interior 8 of the plug-in sleeve 7 preferably comprises at least one circumferential depression 21. These circumferential depressions 21 are implemented as complementary to the ring-shaped protrusion 14 of the pipette 4, which is spaced apart from the end of the pipette 4. However, an interior 8 of the plug-in sleeve 7 having two circumferential depressions 21, which are implemented as complementary to two ring-shaped protrusions 14,14' of the pipette 4, which are arranged on the receptacle end 19 of the pipette 4 and are spaced apart from one another, is particularly preferred and shown. Such a form-fitted receptacle end 19 of a pipette 4, which is plugged in a form-fitted manner over two circumferential depressions of the interior 8 of the plug-in sleeve 7, having two corresponding complementary circumferential, ring-shaped protrusions is indicated by a dotted line.

If the releasable plug connection between the plug-in sleeve 7 of the transport tool 1 and the pipette 4 of a pipetting system 3 is formed by a form fit, the interior 8 of the plug-in sleeve 7 can be implemented as cylindrical—if this is predefined by the shape of the receptacle end 19 of the pipette 4. In this case, the first internal diameter c of the interior 8 would correspond to the second diameter of the interior 8. This situation is also shown for the transport tool 1 in the position C of FIG. 4. To make it easier to insert the pipette 4 through the receptacle opening 10 of the plug-in sleeve 7 into its interior 8, it can be provided that the plug-in sleeve 7 comprises a slot 40 which, originating from the receptacle opening 10, extends in the direction of the connecting part 25, but does not reach it. The length and width of this slot 40 are preferably selected in this case so that, on the one hand, the pipette 4 can be inserted easily into the interior 8 of the plug-in sleeve 7, but the plug-in sleeve 7 is not spread apart in this case so much that the pipette 4 no longer holds the transport tool 1 when it is moved upward again, for example. The form-fitted plug connection must still be able to be formed. On the other hand, this slot 40 can be implemented so that it is used as a replacement for one or more ventilation holes 28, in that it thus itself enables a pressure equalization in the interior 8 of the plug-in sleeve 7 when the pipette 4 is inserted with its receptacle end 19 into the plug-in sleeve 7.

The transport tool 1 shown in the position C additionally comprises reinforcement struts 20 on its plug-in sleeve 7, which extend essentially over the entire length $L_7$ (cf. FIG. 2). Such long reinforcement struts 20 are used for additionally stabilizing the plug-in sleeve 7, if they comprise the long slot 40 to make it easier to insert the pipette 4. The selection of the length, width, and number of such reinforcement struts is within the knowledge of a person skilled in the art.

The at least one holding means 13 of the article holder 11 of the transport tool 1 shown in the position C is implemented, as described above in FIGS. 1A, 1B, 2 and 3, as essentially spherical and slotted. In this case, it is plugged into a storage opening 5' of the pipette tip carrier 2', which spreads apart conically in the direction of the bottom side 24 of the pipette tip carrier 2' originating from the top side 23 of the pipette tip carrier 2'.

The plugged-in transport tool 1 shown in the position E comprises a plug-in sleeve 7, as was already shown for transport tools 1 in FIGS. 1A, 1B, 2 and 3; it is accordingly implemented to form a friction-locked, releasable plug connection with a corresponding receptacle end 19 of a pipette 4. The ventilation hole 28 is located in the connecting part 25 in this case.

The article holder 11 of this transport tool 1 in the position E comprises at least two holding means 13 here, which are implemented as finger-shaped. This finger-shaped holding means 13 completely penetrates the storage opening 5' in this case when the article holder 11 is plugged in, and at least one of these fingers is a finger-shaped snap hook having a stop.

The plug connection between the article holder 11 and the pipette tip carrier 2' is formed in this case at least by means of this finger-shaped snap hook, since, when the article holder 11 is plugged into the storage opening 5', the snap hook is applied to its bottom side 24. A snap connection is thus formed between the finger-shaped holding means 13 and the pipette tip carrier 2'.

In each of these three different embodiments, the sleeve axis 9 of the plug-in sleeve 7, the holding axis 12 of the article holder 11, and the longitudinal axis of the pipette 4 are arranged coaxially to one another in each case when the transport tool 1 is plugged with its plug-in sleeve 7 onto the corresponding receptacle end 19 of the pipette 4 and is plugged with its article holder 11 into a storage opening 5' of a pipette tip carrier 2'. Alternative arrangements are shown in following FIG. 5.

FIG. 5 shows a transport tool 1 according to the invention according to further alternative embodiments with respect to the implementation of its article holder 11. In both of these two embodiments shown, the transport tool 1 comprises two article holders 11 in each case, which are arranged differently with their holding axes 12 with respect to the sleeve axis 9 of the plug-in sleeve 7. The transport tool 1 shown on the left side of FIG. 5 comprises two article holders 11, which are connected by the connecting part 25 to the plug-in sleeve 7 so that the holding axis 12 of the first article holder 11 (the right article holder 11 in this illustration) is arranged coaxially to the sleeve axis 9 and the holding axis 12 of the second article holder 11 (the left article holder 11 in this illustration) is arranged axially-parallel to the sleeve axis 9.

The transport tool 1 shown on the right side of FIG. 5 also comprises two article holders 11. In this case, however, the article holders 11 are connected by the connecting part 25 to the plug-in sleeve 7 so that their two holding axes 12 are axially-parallel to the sleeve axis 9.

The variant of the article holder 11 having the slotted, essentially spherical embodiment of the holding means 13 is shown as an example of this embodiment of the transport tool 1. However, it also applies for this embodiment having two article holders 11 that other variants of the article holder 11 and its at least one holding means 13 can also be used, as long as they are capable of forming a plug connection with free storage openings 5' of a pipette tip carrier 2'.

It is also conceivable that a transport tool 1 not only comprises two, but rather if needed even more article holders 11. If two or more article holders 11 are used per transport tool 1, the axial spacing between the holding axes 12 preferably corresponds to the axial spacing of directly or diagonally adjacent storage openings 5' of the pipette tip carrier 2' to be received.

The use of two or more article holders 11 per transport tool 1 is preferable in particular if, for example, the load which can be lifted is to be increased, or if the holding force of the individual article holders 11 is to be reduced with equal load to be carried.

In a particularly preferred embodiment, the transport tool 1 is produced in one piece and from plastic. To base the properties of the transport tool as closely as possible on the properties of a disposable pipette tip 6 which can be plugged on well for a specific receptacle end 19 of a pipette 4, the same plastic is preferably used for the production of the transport tool 1 as for this disposable pipette tip 6. As an example, polypropylene is mentioned here, which can optionally be admixed with graphite particles. The use of graphite particles is known from the production of disposable pipette tips 6 to make them conductive.

In a very particularly preferred embodiment, the transport tool 1 is used as a disposable article. It is then thus not provided that a transport tool 1 plugged once into at least one storage opening 5' of a pipette tip carrier 2' is released from these storage openings 5' again.

The various embodiments described in the Figures of the plug-in sleeve 7, connecting part 25, and article holder 11 having a holding means 13 can be combined as needed with one another to form an individual transport tool 1, to adapt both to a specific pipette 4 and also to a specific laboratory article 2, for example, a pipette tip carrier 2'.

If the transport tool 1 is essentially adapted in its dimensions and properties, for plugging onto a pipette 4 of a pipetting system 3, to the dimensions and properties of known disposable pipette tips 6, an essential advantage is that the device settings for receiving a disposable pipette tip 6 can also be assumed for receiving a transport tool 1. In addition, a plugged-on transport tool 1, for example, if it has already been used for repositioning an empty pipette tip carrier 2', can also be pushed off of the pipette 4 using the same discarding mechanism and the same device settings. FIG. 6A shows an overview drawing of a possible principle of how a discarding mechanism 30 of a pipetting system 3 for disposable pipette tips 6 can also be used to discard a transport tool 1 plugged onto the pipette 4. In this case, the situation is shown on the left side of FIG. 6A in a first step, in which a transport tool 1 is plugged onto a pipette 4, and additionally a pipette tip carrier 2' having at least 5 free storage openings 5' hangs on its article holder 11. The discarding mechanism 30 of the pipetting system 3 comprises a discarding lever 38 and is arranged in this case on the right adjacent to the pipette 4. The discarding mechanism 30 is pivotable about an axis (not shown), so that it can apply its discarding lever 38 to the top edge of the transport tool 1 (in this case its collar 29) when it is moved into a corresponding discarding position. The pivot direction in which the discarding lever 38 must be moved to actually be applied to the top edge of the transport tool 1, so that the tool 1 is pushed off of the pipette 4, is indicated by a curved arrow. The discarding mechanism 30 can also be pivoted back into it starting position, this pivot direction is not shown in FIGS. 6A and 6B, however. For the discarding, the discarding lever 38 is thus pivoted with the discarding mechanism 30 in the direction of the pipette 4 and moved into the discarding position. The pipette 4 is subsequently moved upward. This upward movement of the pipette 4 is indicated in the situation on the right side of FIG. 6A by a straight arrow.

The pivoting movement of the discarding mechanism 30 and the upward movement of the pipette 4 are preferably adapted to one another so that the discarding lever 38 is applied to the collar 29 of the transport tool 1 when the pipette 4 is still in the upward movement. If the pipette 4 is moved upward, and the discarding lever 38 of the discarding mechanism 30 is already in the discarding position, the plugged-on transport tool 1 is initially also moved upward with the pipette, specifically until it strikes with its top edge against the discarding lever 38. If the pipette 4 is moved further upward, the transport tool 1 is no longer carried along, since it is held by the discarding lever 38 in a fixed vertical position. During a further upward movement of the pipette 4, it is therefore also moved in relation to the transport tool 1, so that the receptacle end 19 of the pipette 4 is pulled out of the plug-in sleeve 7 of the transport tool 1 through the receptacle opening 10. The plug connection is thus released and the transport tool 1 falls—with coupled pipette tip carrier 2' (or here with coupled microplate 2''')— off of the receptacle end 19 of the pipette 4 and downward. This situation is shown on the right side in FIG. 6A.

Similarly thereto, the same discarding mechanism 30 is shown in FIG. 6B as in FIG. 6A. It is used here, as is known from the prior art, for a disposable pipette tip 6 plugged onto a pipette 4 of the pipetting system 3. The discarding mechanism 30 is not yet pivoted in the direction of the pipette 4, but rather is still located in its idle position. To discard the disposable pipette tip 6, the discarding lever 38 is moved its discarding position, so that when the pipette 4 is moved upward, the discarding lever 38 is applied to the top edge of the disposable pipette tip 6 and releases the disposable pipette tip 6 from the pipette 4 during the further upward movement of the pipette.

The situations for a disposable pipette tip 6 and a transport tool 1, which are plugged in a friction-locked manner onto the receptacle end or onto the receptacle cone 19 of the pipette 4, are shown in each of FIGS. 6A and 6B. The principle of the discarding is also transferable to disposable pipette tips 6 and transport tools 1 which are plugged on in a form-fitted manner, however.

In an alternative embodiment of the discarding mechanism 30, which is also known from the prior art, the discarding lever 38 is not directly applied to a top edge of the disposable pipette tip 6 or the transport tool 1, but rather to a top edge of an adapter housing (not shown) which is arranged above the pipette 4 and enclosing it. This adapter housing is elastically movable in relation to the pipette 4 itself. The discarding lever 38 of the discarding mechanism is thus arranged higher in relation to the receptacle end 19 of the pipette 4 in this case. If the discarding lever 38 is pivoted into the discarding position, and the pipette 4 is moved upward by a robot drive, the discarding lever 38 is applied to the top edge of the adapter housing and holds it and an outer sleeve 41 arranged underneath in a specific vertical position. If the pipette 4 is then moved further upward, the originally plugged-on transport tool 1 or the originally plugged-on disposable pipette tip 6 is also initially held by means of the adapter housing and the outer sleeve 41 in a specific vertical position, specifically until the receptacle end 19 is drawn enough out of the interior 8 of the plug-in sleeve 7 that the plug connection is released and the transport tool 1 or the plugged-on pipette tip 6 falls off of the receptacle end 19 and therefore off of the pipette 4.

FIGS. 7A and 7B show vertical sections through two transport tools 1 according to the invention, each having an article holder 11 implemented to form an adhesive bond.

FIG. 7A shows a first variant having a ring-shaped adhesive means 35', which is applied to a flat holding plate 35 aligned essentially perpendicularly to the sleeve axis 9. The adhesive means 35' in the form of a pressure-sensitive adhesive, which was previously applied to both the holding plate 35 and also to a flat surface 42 of a microplate cover 2'', provides the support connection between the microplate cover 2'' and the holding plate 35 of the transport tool 1. The transport tool 1 is plugged onto the receptacle end 19 of a pipette 4, as was already shown and described in conjunction with FIGS. 1A and 1B to 3, wherein the pipette 4 plunges by a plunging depth h' into the plug-in sleeve 7 of the transport tool 1. The holding axis 12 of the article holder 11 and the longitudinal axis 16 of the pipette 4 are arranged coaxially to one another. The transport tool/microplate cover combination 1,2'' which is provided by this adhesive bond can be transported using the pipette 4 of the pipetting system 3 and deposited at arbitrary locations in the region of the work area or the work region of the pipette 4 of this pipetting system 3 and received again as needed. It is therefore possible to lift microplate covers 2'' arbitrarily often off of microplates 2''' and place them thereon again with the aid of a pipette 4.

The preferred position of a tool carrier 37 is indicated by means of a dashed double line. In the case of a stamp-shaped transport tool, a tool carrier 37 is preferred, the design of which is similar to the shape of a stamp carrier (not shown, but known per se to everyone).

FIG. 7B shows a second variant having a circular or square adhesive means 35', which is applied to a flat holding plate 35 aligned essentially perpendicularly to the sleeve axis 9. This holding plate 35 is also the connecting part 25 of the transport tool 1. The transport tool 1 has already been received by a pipette 4 of a pipetting system 3 (cf. FIG. 7A), it is presently still located in the tool carrier 37, on which it rests with its reinforcement struts 20. The adhesive means 35' in the form of a dry adhesive, which was previously glued with a first adhesive side on the holding plate 35, is still covered on the second adhesive side with a protective film 43, which is in turn fastened on the tool carrier 37. If the pipette 4 is now drawn up out of the tool carrier 37, the protective film 43 thus detaches from the second adhesive side of the adhesive means 35' and remains back in the tool carrier 37. The detaching of the protective film 43 from the adhesive means 35' is made easier by an elastic protective film 43 or a transverse fold therein, because the added length of the protective film strip required for the detaching is thus ensured. Subsequently, the pipette 4 can be moved with the transport tool 1 to an arbitrary laboratory article 2 (not shown here) and can be lowered in the region of a flat surface 42 thereof. By lightly pressing the adhesive means 35' onto this flat surface 42, the load-bearing adhesive bond between the transport tool 1 and the laboratory article 2 is produced. The holding axis 12 of the article holder 11 and the longitudinal axis 16 of the pipette 4 are arranged coaxially to one another. The transport tool/laboratory article combination 1, 2 provided by this adhesive bond can be transported using the pipette 4 of the pipetting system 3 and deposited at arbitrary locations in the region of the work area or in the work region of the pipette 4 of this pipetting system 3 and received again as needed. Adhesive bonds between transport tool 1 and laboratory article 2 typically cannot be detached from the pipetting system 3, so that the laboratory article 2 is generally disposed of with glued-on transport tool 1.

FIGS. 8A and 8B show vertical sections through two transport tools 1 according to the invention, each having an article holder 11 implemented to form a magnetic connection.

FIG. 8A shows a first variant having an integrated magnetic means 36' in the form of a cylindrical permanent magnet, which is fastened (for example, glued) with its rear side on the connecting part 25 of the transport tool 1. The permanent magnet (not shown) is preferably enclosed by material of the transport tool 1 for its protection, the permanent magnet can thus also be produced as back-injected with polypropylene in the injection method and thus can be connected to the material of the transport tool 1. Extrusion coating of the permanent magnet with the polypropylene of the transport tool 1 is especially preferred, wherein a thin layer of approximately 0.5 mm to 1 mm polypropylene is preferred on the downwardly-oriented front side of the permanent magnet, so that its attractive force is not excessively reduced (not shown). The permanent magnet preferably has a large field strength and typically comprises rare earth elements such as samarium, cobalt, and/or neodymium. The transport tool 1 has already been received by a pipette 4 of a pipetting system 3 (cf. FIG. 7B), it is presently still located in the tool carrier 37, on which it rests with its reinforcement struts 20. Alternatively, the transport tool 1 can stand with the permanent magnet downward on the tool carrier 37, wherein the latter then only still has a stabilization function and prevents the transport tool 1 from falling over or slip-ping away. The holding axis 12 of the article holder 11 and the longitudinal axis 16 of the pipette 4 are arranged coaxially to one another. The pipette 4 with the transport tool 1 can be lifted out of the tool carrier 37, moved to an arbitrary laboratory article 2 (not shown here), and lowered in the region of a flat surface 42 thereof. The flat surface 42 of the laboratory article 2 to be received is preferably laminated or covered with a foil made of magnetizable material 44 (for example, iron, nickel, or iron/nickel alloys). By lowering the transport tool 1 onto this flat surface 42, the load-bearing magnetic connection between the permanent magnet of the transport tool 1 and magnetizable material 44 of the laboratory article 2 is established. The transport tool/laboratory article combination 1 provided by this magnetic connection can be transported using the pipette 4 of the pipetting system 3 and deposited at arbitrary locations in the region of the work area or in the work region of the pipette 4 of this pipetting system 3 and received again as needed.

FIG. 8B shows a second variant having a magnetic means 36' in the form of a circular or square strip magnet, which is attached (for example, glued) onto a flat holding plate 35 which is aligned essentially perpendicularly to the sleeve axis 9. This holding plate 35 is also the connecting part 25 of the transport tool 1. This holding plate 35 preferably has a substantially larger area than the connecting part 25, because experience has shown that strip magnets have a lower field strength than cylindrical permanent magnets, for example. The transport tool 1 has been received by a pipette 4 of a pipetting system 3 and a load-bearing magnetic connection has already been established between the transport tool 1 and the magnetizable material 44 (for example, a foil having iron, nickel, or iron/nickel alloys) on the surface 42 of a microplate cover 2". Alternatively, the flat surface 42 of the laboratory article 2 to be received is laminated with a second strip magnet (not shown). The transport tool/laboratory article combination 1, 2 provided by this magnetic connection can be transported using the pipette 4 of the pipetting system 3 and deposited at arbitrary locations in the region of the work area or in the work region of the pipette 4 of this pipetting system 3 and received again as needed. The preferred position of a tool carrier 37 is indicated by means of a dashed double line. In the case of a stamp-shaped transport tool, a tool carrier 37, the design of which is similar to the shape of a stamp carrier, is preferred (not shown, but known per se to everyone).

Magnetic connections between transport tool 1 and laboratory article 2 can typically be detached again manually or also automatically by the pipetting system 3, in that the laboratory article 2 is deposited secured against lateral movements, and then the transport tool 1 is drawn off sideways and, for example, in the essentially horizontal direction from the magnetizable material 44 of the laboratory article 2. This simple reuse of the transport tool 1 is a significant advantage of the magnetic connection and allows only the laboratory article 2 to have to be disposed of (if necessary).

Pipette tips 6 as disposable articles can be discarded after use on a waste chute for disposal. However, for repeated use, the pipette tips 6 can also be inserted back into empty storage openings 5' of a pipette tip carrier 2' until the reinforcement struts 26 are located a few millimeters above the top edge of the pipette tip carrier 2'. The pipette tips 6 are then "discarded" or reset, respectively, according to FIG. 6B. The reset and reuse makes sense if the corresponding pipette tips 6 were used to distribute buffer solutions, for example, but not samples. The same basic mechanism can be applied for the targeted depositing and reuse of other laboratory articles 2, for example, covers of microplates 2''', troughs, and the like.

Identical reference signs refer to corresponding elements of the present invention, although reference is not made specifically thereto in each case. Although many of the examples shown refer to pipette tip carriers 2', all findings obtained and features defined in conjunction with the transport tools 1 according to the invention and the use thereof can be applied similarly to receiving, transporting, depositing, or discarding practically any arbitrary laboratory articles 2.

List of reference signs

| | | | |
|---|---|---|---|
| 1 | transport tool | 33 | projection |
| 2 | laboratory article | 34 | outer side of 7 |
| 2' | pipette tip carrier | 35 | holding plate |
| 2" | microplate cover | 35' | adhesive means |
| 2''' | microplate | 36 | holding sleeve |
| 3 | pipetting system | 36' | magnetic means |
| 4 | pipette | 37 | tool carrier, tool holder |
| 5 | opening | 38 | discarding lever |
| 5' | storage opening | 39 | upper edge of 19 |
| 5" | well of 2''' | 40 | slot of 7 |
| 6 | pipette tip | 41 | external sleeve of the pipette 4 |
| 7 | plug-in sleeve | | |
| 8 | interior of 7 | 42 | flat surface of 2, 2', 2" |
| 9 | sleeve axis | 43 | protective film |
| 10 | receptacle opening of 7 | 44 | magnetizable material |
| 11 | article holder | a | largest external diameter of 13 |
| 12 | holding axis of 11 | | |
| 13 | holding means | b | smallest external diameter of 25 |
| 14, 14' | ring-shaped protrusion | | |
| 15 | longitudinal axis of 6 | c | first internal diameter of 8 |
| 16 | longitudinal axis of 4 | d | second internal diameter of 8 |
| 17 | receptacle opening of 6 | e | smallest internal diameter of 5, 5' |
| 18 | neck part of 1 | | |
| 19 | receptacle end, cone of 4 | f,f' | outer internal diameter of 5, 5' |
| 20, 20' | reinforcement struts of 1 | | |
| 21 | depression for 14 | g | plug-in depth of 1 |
| 22 | slot | h, h' | plunging depth of 4 |
| 23 | top side of 2, 2', 2" | i | external diameter of 14 |
| 24 | bottom side of 2, 2', 2" | k | external diameter of 14' |
| 25 | connecting part | l | length ($l_6$, $l_7$, $l_{11}$, $l_{13}$, $l_{14-14'}$, $l_{25}$, $l_{35}$, $l_e$) |
| 26 | reinforcement strut of 6 | | |
| 27 | interior of 6 | m | first internal diameter of 6 |
| 28 | ventilation hole | n | second internal diameter of 6 |
| 29 | collar of 7 | o | first external diameter of 6 |
| 30 | discarding mechanism | p | second external diameter of 6 |
| 31 | side wall of 7 | q | external diameter of 19 |
| 32 | outer side of 11 and 13 | r | internal diameter of storage opening of 37 |

What is claimed is:

1. A transport tool for transporting a laboratory article using a pipette of a pipetting system, the transport tool comprising:
   a plug-in sleeve at a top end of the transport tool;
   an article holder at a bottom end of the transport tool; and
   a connecting part which connects the plug-in sleeve to the article holder;
   wherein the transport tool is vertically elongated along a vertical axis;
   wherein the plug-in sleeve comprises a side sleeve wall and a bottom, wherein the side sleeve wall has an inner surface and an outer surface, and wherein the side sleeve wall and the bottom surround an interior space of the plug-in sleeve;
   wherein said interior space of the plug-in sleeve has a shape selected from: cylindrical and conically tapering;
   wherein the plug-in sleeve comprises an upward-facing opening, the upward-facing opening being positioned to receive an end of a pipette of an automated pipetting system into the interior space of the plug-in sleeve;
   wherein the connecting part is positioned between the interior space of the plugin sleeve and the article holder, and said top surface of the connecting part is located at a lower end of the plug-in sleeve opposite the upward-facing opening; and
   wherein the article holder comprises a holding element oriented downward away from the connecting part, the holding element being shaped for insertion into and friction connection with a storage opening of a pipette tip carrier, the holding element having a spherical shape.

2. The transport tool of claim 1:
   wherein the side sleeve wall of the plug-in sleeve tapers towards the connecting part, the interior space of the plug-in sleeve having a wider end and a narrower end, wherein the upward-facing opening is at the wider end of the plug-in sleeve.

3. The transport tool of claim 1:
   wherein the side sleeve wall of the plug-in sleeve comprises a circumferential depression in the inner surface shaped for engagement with a complementary protrusion of the end of the pipette.

4. The transport tool of claim 1:
   wherein the holding element of the article holder has at least one slot which extends upwards from the bottom end of the transport tool, said at least one slot providing a spring function to the holding element for a friction-lock insertion into a storage opening of a pipette tip carrier.

5. The transport tool of claim 1:
   further comprising at least one ventilation hole in the side wall of the plug-in sleeve or in the connecting part.

6. The transport tool of claim 1:
   wherein exactly one article holder is provided at the bottom end of the transport tool; and
   wherein said vertical axis of the transport tool passes through a center of the plug-in sleeve and a center of the exactly one article holder, with the plug-in sleeve being positioned directly above the article holder.

7. The transport tool of claim 1:
   wherein the transport tool comprises a first article holder and a second article holder positioned beside each other.

8. The transport tool of claim 7:
   Wherein the first article holder and the second article holder are positioned side-by-side, and are spaced apart by a distance corresponding to a distance between one of: two storage openings of a pipette tip carrier for use with the transport tool, or two wells of a microplate for use with the transport tool.

9. The transport tool of claim 1:
   wherein the transport tool, including the plug-in sleeve, the article holder, and the holding element are collectively formed as a single piece of plastic.

10. The transport tool of claim 1:
    wherein said connecting part comprises a connecting wall, the connecting wall being oriented so that said vertical axis of the transport tool is perpendicular to the connecting wall.

11. A method for transporting a pipette tip carrier using a pipette of an automated pipetting system, the method comprising:
    providing a transport tool according to claim 1;
    providing a pipette tip carrier comprising a storage opening;

providing an automated pipetting system comprising at least one pipette;

inserting the at least one pipette of the automated pipetting system into the plug-in sleeve of the transport tool, with the at least one pipette reversibly engaging the plug-in sleeve;

inserting the holding element of the transport tool into the storage opening of the pipette tip carrier, and the holding element thereby engaging the pipette tip carrier;

after said engaging of the at least one pipette with the plug-in sleeve of the transport tool, and after said engaging the holding element of the transport tool with the storage opening of the pipette tip carrier; and moving the at least one pipette and thereby moving the pipette tip carrier, with the transport tool linking the at least one pipette and the pipette tip carrier.

12. The method according to claim 11, the method further comprising:

after said moving of the pipette tip carrier, disengaging the at least one pipette of the automated pipetting system from the plug-in sleeve of the transport tool, and thereby also unlinking the at least one pipette from the pipette tip carrier.

13. The method according to claim 11, the method further comprising:

after moving the pipette tip carrier, disengaging the holding element of the transport tool from the storage opening of the pipette tip carrier.

14. The method according to claim 11:

wherein the at least one pipette of the automated pipetting system comprises a tip discarding mechanism, for ejecting disposable pipette tips from the pipette after use;

the method further comprising the step of:

after moving the pipette tip carrier by moving the at least one pipette, ejecting the transport tool from the at least one pipette using the tip discarding mechanism, wherein said ejecting of the transport tool comprises disengaging the at least one pipette from the plug-in sleeve of the transport tool;

wherein said ejecting the transport tool from the at least one pipette also functions to disengage the pipette tip carrier from the at least one pipette.

* * * * *